(12) United States Patent
van Maris et al.

(10) Patent No.: US 7,405,068 B2
(45) Date of Patent: Jul. 29, 2008

(54) PYRUVATE PRODUCING YEAST STRAIN

(75) Inventors: Antonius Jeroen Adriaan van Maris, Decatur, IL (US); Jacobus Thomas Pronk, Schipluiden (NL); Johannes Pieter van Dijken, Leidschendam (NL)

(73) Assignee: Tate & Lyle Ingredients Americas, Inc., Decatur, IL (US)

( * ) Notice: Subject to any disclaimer, the term of this patent is extended or adjusted under 35 U.S.C. 154(b) by 277 days.

(21) Appl. No.: 10/835,611

(22) Filed: Apr. 29, 2004

(65) Prior Publication Data

US 2005/0059136 A1    Mar. 17, 2005

(51) Int. Cl.
*C12N 1/19* (2006.01)
*C12N 1/18* (2006.01)

(52) U.S. Cl. ............... 435/254.21; 435/255.2

(58) Field of Classification Search ............... None
See application file for complete search history.

(56) References Cited

U.S. PATENT DOCUMENTS

| | | | | |
|---|---|---|---|---|
| 5,866,371 | A | 2/1999 | Badziong et al. | 435/69.2 |
| 6,001,255 | A | 12/1999 | Eyal et al. | 210/638 |
| 6,043,072 | A | 3/2000 | Croteau et al. | 435/193 |
| 2003/0166179 | A1 | 9/2003 | Rajgarhia et al. | 435/139 |
| 2003/0190630 | A1 | 10/2003 | Rajgarhia et al. | 435/6 |

FOREIGN PATENT DOCUMENTS

| WO | WO98/15518 | 4/1998 |
|---|---|---|
| WO | WO00/71738 | 11/2000 |
| WO | WO02/42471 | 5/2002 |

OTHER PUBLICATIONS

Zulli et al., *Biol. Chem. Hoppe-Seyler* 368:1167-1177 (Sep. 1987).
Waldvogel et al., *Biol. Chem. Hoppe-Seyler* 368:1391-1399 (Oct. 1987).
Kim et al., *Applied and Environmental Microbiology* 57(8):2413-2417 (Aug. 1991).
Hohmann, "Pyruvate Decarboxylases," Chapter 11, *Yeast Sugar Metabolism*, pp. 187-211 (1997).
NCBI GenBank Accession No. AJ293008 (Aug. 3, 2004).
PCT/US04/13495 International Search Report (Nov. 19, 2004).
van Maris et al., *Applied and Environmental Microbiology* 70(1):159-166 (Jan. 2004).
Flikweert et al., *Yeast* 12:247-257 (1996).
Flikweert et al., *FEMS Microbiology Letters* 174:73-79 (1999).
Flikweert et al., *Applied and Environmental Microbiology* 63(9):3399-3404 (Sep. 1997).

*Primary Examiner*—Nancy Vogel
(74) *Attorney, Agent, or Firm*—Williams, Morgan & Amerson, P.C.

(57) ABSTRACT

Disclosed herein are glucose tolerant $C_2$ carbon source-independent (GCSI) yeast strains having no detectable amount of pyruvate decarboxylase activity, wherein wild type yeast strains for the glucose tolerant $C_2$ carbon source-independent yeast strains are Crabtree positive. Also disclosed are methods of selecting glucose tolerant $C_2$ carbon source-dependent yeast strains, and methods of producing pyruvic acid or salts thereof using glucose tolerant $C_2$ carbon source-independent yeast strain. Further disclosed herein are GCSI yeast strains having a genome that comprises an exogenous lactate dehydrogenase gene.

3 Claims, 14 Drawing Sheets

PYRUVATE PRODUCING YEAST STRAIN

BACKGROUND OF THE INVENTION

1. Field of the Invention

The present invention relates generally to yeasts derived from Crabtree positive yeasts, wherein the yeasts produce relatively high concentrations of pyruvic acid or salts thereof when grown in an aerobic environment with glucose, without producing a significant amount of ethanol. The present invention relates to Crabtree positive yeasts, such as *Saccharomyces cerevisiae*, that lack pyruvate decarboxylase activity, and that are capable of growing in an aerobic environment in mineral medium having glucose or other sugars to produce pyruvic acid or salts thereof. The present invention also relates to yeasts, which, when cultured, can produce relatively high concentrations of lactic acid.

2. Description of Related Art

It is known in the art that certain *Saccharomyces cerevisiae* strains can be used to rapidly ferment sugars to ethanol and carbon dioxide both in an anaerobic environment, and in an aerobic environment in the presence of excess carbohydrates (e.g., glucose). In addition to ethanol, *Saccharomyces cerevisiae* and certain other fungi can be used in the production of certain other chemical compounds of commercial value. It is desirable to maximize the product yield and/or concentration in commercial processes. Toward this end, one method that has been used involves the redirection of carbon flux away from alcoholic fermentation, and toward production of the desired product.

Recovery of pyruvic acid (and salts thereof), a common intermediate in sugar metabolism of all living cells, is of commercial interest. Pyruvic acid or salts thereof can be used as a starting material in the chemical synthesis of certain pharmaceuticals. Pyruvic acid and salts thereof can also be useful in the production of certain crop protection agents, polymers, cosmetics, and food additives. There is some evidence that suggests pyruvate may also have health benefits for humans. In addition, certain commercially valuable chemicals can be biochemically-derived from pyruvic acid or salts thereof. For example, lactate or alanine can each be produced from pyruvic acid by a single enzymatic reaction. Similarly malate can be produced by a two step enzymatic reaction.

Yeasts, like *Saccharomyces cerevisiae*, have drawn attention as good organisms for the production of pyruvic acid, salts thereof, and its chemical derivatives from sugars or carbohydrate feed stocks. This is because the yeasts combine the desirable properties of high glycolytic fluxes (e.g., relatively high rates of pyruvic acid formation), and acid tolerance.

In certain yeasts, notably Crabtree positive yeasts, the main pathway for decarboxylation when the yeasts are grown with an excess of a carbon source involves pyruvate decarboxylase. Crabtree positive yeasts produce alcohol from pyruvate in the presence of excess sugar (e.g., glucose) under aerobic conditions or when the specific growth rate of the culture is higher than the critical specific growth rate. Examples of Crabtree positive yeasts are found among *Saccharomyces cerevisiae, Candida glabrata* (also known as *Torulopsis glabrata*, among other names known in the art), *Zygosaccharomyces bailii* and *Schizosaccharomyces pombe*. In facultative fermentative yeast (e.g., yeast that can thrive on alcoholic fermentation or respiration or both) pyruvate decarboxylation can occur via two enzymes: the pyruvate dehydrogenase complex and/or pyruvate decarboxylase. In order to redirect carbon flux away from ethanol production to improve the yield and concentration of pyruvate and its derivatives in a culture, it is desirable to limit the decarboxylation of pyruvic acid.

In *Saccharomyces cerevisiae* pyruvate decarboxylase (EC 4.1.1.1) catalyzes the conversion of pyruvate to acetaldehyde, and this is the first step in fermentative sugar metabolism. It has been proposed that in addition to its catabolic activity, pyruvate decarboxylase also serves a biosynthetic function. It is known in the art that certain pyruvate decarboxylase negative (Pdc negative) (e.g., having no detectable amount of pyruvate decarboxylase activity) *Saccharomyces cerevisiae* strains cannot grow on synthetic medium in an aerobic glucose-limited chemostat, when glucose is the sole carbon source, without the addition of small amounts of ethanol or acetate (e.g., 5% of carbon required for growth). Such Pdc negative *Saccharomyces cerevisiae* strains are also known not to grow, even in the presence of small amounts of ethanol or acetate, in batch cultures on synthetic culture medium with glucose as the only other carbon source. In contrast to this, Crabtree negative yeasts that have no pyruvate decarboxylase activity, exhibit no such growth requirements when grown aerobically on sugars.

It is further known in the art that overproduction of threonine aldolase (EC 4.1.2.5) in yeast, can under certain conditions, circumvent the loss of the biosynthetic activity of pyruvate decarboxylase in Pdc negative *Saccharomyces cerevisiae*, in that the Pdc negative threonine aldolase overexpressing *Saccharomyces cerevisiae* can grow in an aerobic sugar-limited chemostat. However, threonine aldolase overproducing strains lacking pyruvate decarboxylase activity have impaired growth at high sugar concentrations.

Lactic acid (2-hydroxypropionic acid, $CH_3CHOHCOOH$) is a naturally occurring hydroxyl acid that can be produced by fermentation or chemical synthesis. Lactic acid can be used in food as a preservative and flavor enhancer. Lactic acid derivatives can be used in industrial applications, such as paint and electrodeposition coating, pharmaceuticals and cosmetics. An important compound that can be produced by the dehydration of lactic acid is poly(lactic acid) plastic.

Wild type *S. cerevisiae* transformed with a lactate dehydrogenase-bearing (e.g., LDH-bearing) plasmid can produce some lactic acid when cultured. Preferably lactic acid is recovered and purified to the highest possible level of purity when used as a polymer grade feedstock. The organic impurities (derived from complex nitrogen sources, for example), the inorganic impurities (related to media ingredients and neutralizing agents), and the metabolic intermediates secreted by the production organism during fermentation are preferably all removed.

SUMMARY OF THE INVENTION

In certain embodiments, the present invention is directed to *Saccharomyces cerevisiae* yeast strains and certain other Crabtree positive yeast strains that have no detectable amount of pyruvate decarboxylase activity, and that can grow in an aerobic batch culture on synthetic medium with relatively high concentrations of glucose as the sole carbon and energy source to produce relatively high concentrations of pyruvic acid and salts thereof. Employing certain embodiments of the present invention, such yeast strains can be obtained without using targeted metabolic engineering In certain embodiments the yeasts do not have a higher level of threonine aldolase activity than a wild type strain.

Certain embodiments of the present invention are directed to a glucose tolerant, $C_2$ carbon source-independent (GCSI) yeast strain that has no detectable amount of pyruvate decarboxylase activity, wherein a wild type yeast strain for the GCSI yeast strain is Crabtree positive. In certain embodiments, a GCSI yeast strain can be capable of growing in a culture medium comprising at least one carbon source selected from the group consisting of glucose, sucrose, fructose, maltose, hydrolyzed starch, galactose, high fructose corn syrup, lactose, and hydrolyzed lignocellulose, among others. Certain GCSI yeast strains of the present invention can be capable of producing a concentration of at least about 0.5 moles pyruvic acid per liter when cultured in an aerobic batch culture in a synthetic medium. In some embodiments, the GCSI yeast strain can be a *S. cerevisiae* yeast. In other embodiments the GCSI yeast strain can be a *Candida glabrata*. Certain GCSI *Candida glabrata* yeast strains of the present invention can be capable of producing greater than about 700 mM pyruvic acid or salts thereof, when cultured in mineral medium comprising a sugar (e.g., glucose) that can be used as a carbon source by the *Candida glabrata* yeast strains.

Certain embodiments of the present invention are directed to methods of selecting a GCSI yeast strain, and other embodiments are directed to yeast strains that can be selected using such methods. The selection methods can comprise growing a yeast culture in an aerobic carbon-limited chemostat. The yeast culture is started by inoculating a first mineral medium with a Pdc negative yeast strain. A wild type yeast strain for the Pdc negative yeast strain is Crabtree positive. The Pdc negative yeast strain can be derived when pyruvate decarboxylase activity is eliminated in the wild type yeast strain.

At the start of growing the culture, the first mineral medium can comprise glucose and a $C_2$ carbon source as the sole carbon sources, concentrations of the two carbon sources are sufficient to permit growth of the yeast culture. During growth of the yeast culture in the chemostat the concentration of the $C_2$ carbon source in the feed medium can be lowered until the concentration of the $C_2$ carbon source is in a target range between about 10% and 0% of total carbon.

At least one $C_2$ carbon source-independent yeast strain can be recovered from the chemostat yeast culture once the concentration of the $C_2$ carbon source reaches the target range. The recovered $C_2$ carbon source-independent yeast strain has no detectable amount of pyruvate decarboxylase activity. The $C_2$ carbon source-independent yeast strain can then be cultured in a single aerobic batch culture or a series of aerobic batch cultures using a second mineral medium. Glucose can be the sole carbon source in the batch cultures, and the concentration of glucose can be increased over the series of batch cultures. The concentration of glucose in the batch culture or the initial batch culture that begins the series can be such that it permits growth of the $C_2$ carbon source-independent yeast strain. Starting with "an amount of glucose that permits growth" can, in effect, amount to the initial selection for glucose tolerance. Since, in certain embodiments, the $C_2$ carbon source-independent yeast strain cannot grow on even low levels of glucose as the sole carbon source, until a $C_2$ carbon source-independent yeast strain mutates, and begins to grow in the presence of glucose in the batch culture. A mutant that has been selected can be capable of growing with glucose as the sole carbon source. In a series of batch cultures each successive batch culture can be seeded with yeast grown in a batch culture from earlier in the series.

At least one GCSI yeast strain can be recovered from a batch culture of the series of batch cultures. The GCSI yeast strain is capable of growing without a $C_2$ carbon source, and with glucose as a sole carbon source. The recovered GCSI yeast strain is more glucose tolerant than the recovered $C_2$ carbon source-independent yeast strain, and the GCSI yeast strain has no detectable amount of pyruvate decarboxylase activity. In certain embodiments, the GCSI yeast strain comprises (A) at least one PDC structural gene that is capable of being expressed in the wild type yeast strain; (B) at least one PDC regulatory gene that is capable of being expressed in the wild type yeast strain; (C) a promoter of the PDC structural gene; and (D) a promoter of the PDC regulatory gene. At least one of (A)-(D) can be (i) mutated, (ii) disrupted, or (iii) deleted. Mutation, disruption or deletion of at least one of (A)-(D) can, in certain embodiments, contribute to the lack of pyruvate decarboxylase activity.

Certain embodiments are directed to methods of selecting a glucose tolerant $C_2$ carbon source-independent (GCSI) yeast strain and the GCSI yeast strains selected using such methods. The methods can comprise inoculating a mineral medium with a Pdc negative yeast strain (e.g., Pdc negative yeast as described above). The Pdc negative yeast strain can be cultured aerobically. At the start of growing the yeast culture, the mineral medium comprises glucose and a $C_2$ carbon source as the sole carbon sources in sufficient concentrations to permit growth of the yeast culture. The concentration of the $C_2$ carbon source is decreased as the yeast culture grows until the culture is capable of growth without a $C_2$ carbon source. The concentration of glucose is increased as the yeast culture grows. Finally, at least one GCSI yeast strain lacking pyruvate decarboxylase activity can be recovered. In certain embodiments, the step of decreasing the concentration of the $C_2$ carbon source, and the step of increasing the concentration of glucose can be performed simultaneously, preferably the simultaneous steps are performed in an aerobic chemostat. In other embodiments, the step of increasing the concentration of the glucose is performed before the step of decreasing the concentration of the $C_2$ carbon source, and the steps are preferably performed in an aerobic chemostat. In still other embodiments, decreasing the concentration of the $C_2$ carbon source is performed before the step of increasing the concentration of the glucose. When the decreasing step is performed first, both the increasing and decreasing steps can, in certain embodiments, be performed in a chemostat(s), or alternatively, the decreasing step can be done in a chemostat, and the increasing step can be performed over a series of batch cultures.

Certain embodiments of the present invention are directed to methods of producing pyruvic acid or salts thereof. The method involves aerobically culturing a glucose tolerant $C_2$ carbon source-independent (GCSI) yeast strain in a first culture medium to produce pyruvic acid or salts thereof. The wild type strain for the GCSI yeast strain is Crabtree positive. The first culture medium can comprise at least one carbon source selected from the group consisting of glucose, sucrose, fructose, maltose, lactose, galactose, hydrolyzed starch, high fructose corn syrup and hydrolyzed lignocelluloses, among others. In certain embodiments, when the GCSI yeast strain is cultured in an aerobic batch culture in the first culture medium, at least about 1.53 moles pyruvic acid per liter can be produced. The first culture medium can be a mineral medium, in certain embodiments, especially a mineral medium comprising glucose as a sole carbon source. The pyruvic acid or salt thereof that is produced can be further purified using methods known in the art.

Certain embodiments of the present invention are directed to a GCSI yeast strain, as described above, that comprises a genome that comprises an exogenous lactate dehydrogenase gene that is capable of being expressed in the GCSI yeast strain. A protein resulting from the expression of the exogenous lactate gene has lactate dehydrogenase activity. In some embodiments, the GCSI yeast strain having the exogenous lactate dehydrogenase gene (GCSI-L) is capable of producing greater than about 70 grams of lactic acid/100 grams glucose when cultured in a minimal medium comprising glucose as a sole carbon source. The GCSI-L strain can be a *Saccharomyces cerevisiae* having a genotype pdc1(−6,−2)::loxP pdc5(−6,−2)::loxP pdc6(−6,−2)::lox P ura3-52 YEpLpLDH, in certain embodiments. In some embodiments, the exogenous lactate dehydrogenase gene can be a *Lactobacillus plantarum*, bovine, *Lactobacillus casei, Bacillus megaterium, Rhizopus oryzae*, or *Bacillus stearothermophylus* lactate dehydrogenase gene. Examples of nucleotide sequences of such genes are available on Genbank under accession numbers AJ293008, NP 776524, M76708, M22305, Q9P4B6, and M19396, respectively. The GCSI yeast strain having the exogenous LDH can, in certain embodiments, be capable of producing greater than about 100 gl$^{-1}$ lactic acid in a culture broth, when cultured aerobically in a minimal medium. In some embodiments, a GCSI yeast strain having an exogenous LDH can be capable of producing lactic acid consisting essentially of L-lactic acid.

Certain embodiments, of the present invention are directed to methods of producing lactic acid or salts thereof. The methods comprise aerobically culturing in a first culture medium a GCSI-L yeast strain The GCSI yeast strain comprising the exogenous LDH can be capable of producing at least about 70 grams lactic acid/100 grams glucose when grown in a minimal medium comprising glucose as the sole carbon source.

DESCRIPTION OF ILLUSTRATIVE EMBODIMENTS

Figure 1:
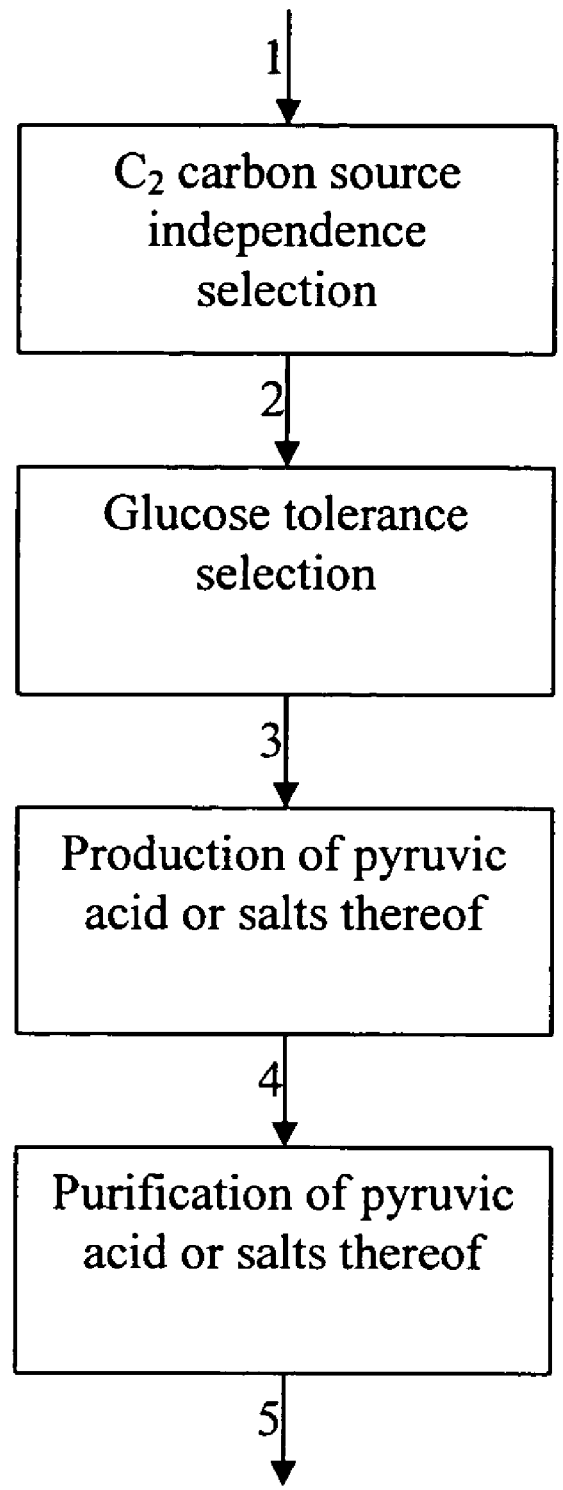
FIG. 1 is a schematic representation of an embodiment of the present invention.

"Pyruvate decarboxylase" (Pdcp) refers to any protein (e.g., enzyme), which can catalyze the conversion of pyruvate to acetaldehyde. "PDC" refers to a particular wild type gene of pyruvate decarboxylase. "pdc" refers to a particular mutant pyruvate decarboxylase gene. "No detectable amount of pyruvate decarboxylase activity" refers to pyruvate decarboxylase activity in yeast that is below the detection limit of 0.005 micromol/min mgprotein$^{-1}$ when using the methods previously described (24): Pyruvate decarboxylase activity can be reduced or essentially eliminated from a yeast strain using methods known in the art. For example, a pyruvate decarboxylase structural gene, a pyruvate decarboxylase structural gene's promoter, a gene that regulates the pyruvate decarboxylase structural gene expression, or a promoter of the regulatory gene can be mutated, disrupted, or at least a portion of the gene can be deleted. This can result in reduced pyruvate decarboxylase activity or in no detectable amount of pyruvate decarboxylase activity being present in a yeast strain. Still further, the gene expression can be altered using other methods known in the art. For example, an antisense construct can be introduced into a yeast strain that reduces the translation of pyruvate decarboxylase mRNA to pyruvate decarboxylase protein.

"Pdc negative yeast strain" refers to yeast having no detectable pyruvate decarboxylase activity, and that does not grow in an aerobic environment on glucose as a sole carbon source in a synthetic culture medium. At least some Pdc negative strains do not produce detectable amounts of ethanol during growth in an aerobic environment in a mineral medium. A Pdc negative Saccharomyces cerevisiae grown in an aerobic glucose-limited chemostat on synthetic medium requires addition of small amounts of a $C_2$ carbon source (e.g., ethanol, acetaldehyde, and/or acetate). The same Pdc negative Saccharomyces cerevisiae strain will not grow, even in the presence of small amounts of ethanol or acetate, in batch cultures on synthetic medium with glucose as the sole carbon source. The isogenic wild type strain corresponding to the Pdc negative strain is Crabtree positive (see discussion below). The wild type strain has detectable pyruvate decarboxylase activity. A Pdc negative strain that is not capable of growing in culture medium comprising glucose as the sole carbon source can be derived when pyruvate decarboxylase activity is eliminated (e.g., by disruption or mutation of the structural genes, or disruption of the regulation of gene expression, among others) from the wild type strain.

"Lactate dehydrogenase" (Ldhp) refers to a protein (e.g., enzyme), which catalyzes the conversion of pyruvate to lactate. "LDH" refers to a wild type gene that when expressed yields a protein that has lactate dehydrogenase activity. "ldh" refers to a mutant lactate dehydrogenase gene. A LDH as used in the present application can include genes that are not named lactate dehydrogenase in the art that when expressed result in a protein having lactate dehydrogenase activity. Lactate dehydrogenase genes can be stereospecific. That is, a lactate dehydrogenase gene may catalyze a reaction to produce only L-lactate or only D-lactate. Other lactate dehydrogenases catalyze a reaction to produce both L- and D-lactate. A L-lactate dehydrogenase gene catalyzes the conversion of pyruvate to L-lactate.

"Wild type yeast" refers to a yeast, which when it has heritable genetic alterations introduced into its genome results in the production of a mutant yeast. Restated the mutant yeast strain has a different genotype than its wild type strain in that certain mutations, deletions or insertions have been introduced into its genome that are not present in the wild type yeast strain's genome. Thus, the wild type yeast strain lacks the changes that are present in the genome of the mutant yeast strain. The mutant yeast strain can, in some cases, have a different phenotype than the wild type strain. The mutant yeast strain can be prepared by methods known in the art, including those involving homologous recombination, directed mutagenesis or random mutagenesis, among others. In certain cases, the mutant yeast strain can be recovered by a process involving natural selection.

"Parent yeast" refers to a yeast from which a new yeast strain is derived directly. For example, a parent strain might comprise a yeast with an exogenous lactate dehydrogenase gene in its genome that requires a $C_2$ carbon source (see below) for growth. An acid tolerant yeast strain having the lactate dehydrogenase gene may be derived from the parent strain through a selection process for acid tolerance. The acid-tolerant $C_2$ carbon source dependent yeast strain may in turn become the parent strain of an acid-tolerant $C_2$ carbon source independent yeast strain having the lactate dehydrogenase gene through a selection process for $C_2$ carbon source independence of the acid-tolerant yeast strain. A parent strain can, in some instances, also be a wild type strain, though this is not a requirement.

"$C_2$ carbon source-independent yeast strain" refers to a yeast having no detectable pyruvate decarboxylase activity that, when cultured on mineral medium having glucose as the sole carbon source, does not require a $C_2$ carbon source. The $C_2$ carbon source-independent yeast strain is derived through manipulation (e.g., selection or site directed mutagenesis, among others) of a Pdc negative parent strain that requires a $C_2$ carbon source to grow in mineral medium in which glucose is the only other carbon source in an aerobic glucose-limited chemostat. The $C_2$ carbon source-independent yeast strain can, in some embodiments, not have a higher level of activity of threonine aldolase than its wild type strain grown under the same conditions.

"Glucose tolerant yeast strain" as used herein refers to a yeast derived from a Pdc negative or $C_2$ carbon source-independent yeast parent strain by a single or multi-step selection process. The glucose tolerant yeast strain has no pyruvate decarboxylase activity. When the glucose tolerant yeast strain and its parent strain are grown on the same mineral medium under the same conditions (e.g., pH, temperature, among others), the glucose tolerant yeast strain can grow on medium having a higher concentration of glucose, than the parent strain can grow on. Alternatively the glucose tolerant yeast strain can grow to a higher cell density than the parent strain (e.g., a Pdc negative strain can be the parent strain of a $C_2$ carbon source-independent yeast strain derived from it), when both are grown on the same medium having the same glucose concentration, when glucose is the sole carbon source, under the same or similar conditions. In another alternative, the glucose tolerant yeast strain can have a higher specific growth rate, than the parent strain, when both are grown on the same medium having the same glucose concentration, when glucose is the sole carbon source, under the same or similar conditions. In certain embodiments of the present invention a glucose tolerant yeast strain that has no pyruvate decarboxylase activity can grow on a mineral medium comprising at least 0.5 g/liter glucose.

"More glucose tolerant" refers to a yeast strain that is capable of growing at higher concentrations of glucose than another yeast strain, when both are grown in essentially the same culture medium having glucose as the sole carbon source under essentially the same conditions. Alternatively, the term can refer to a yeast strain that is capable of growing to a higher culture density than another yeast strain, when both are grown in essentially the same culture medium with essentially the same concentration of glucose, which is the sole carbon source. The more glucose tolerant yeast strain can have a higher specific growth rate, than another yeast strain, when both are grown on essentially the same medium having essentially the same glucose concentration, when glucose is the sole carbon source, under the same or similar conditions "Crabtree effect" is defined as alcoholic fermentation carried out by a yeast strain in (a) an environment comprising excess oxygen and excess sugar (e.g., carbohydrates) (in certain embodiments "excess sugar" is at a concentration above about 1 mM) or (b) a culture in which the specific growth rate of the yeast strain is higher than the critical specific growth rate on glucose (e.g., about two-thirds of the maximum specific growth rate on glucose). A yeast strain is "Crabtree positive," if it exhibits the Crabtree effect, and a Crabtree positive yeast strain, employs the pyruvate decarboxylase route as its main pyruvate decarboxylation pathway in the presence of excess sugar. Examples of Crabtree positive yeasts can be found among *Saccharomyces cerevisiae, Candida glabrata* (also known as *Torulopsis glabrata*, among others), *Zygosaccharomyces* bailii, and *Schizosaccharomyces pombe*, among others. A "Crabtree negative yeast strain" uses the pyruvate dehydrogenase complex reaction as its main mechanism of pyruvate decarboxylation. When growing aerobically with excess sugar alcoholic fermentation hardly occurs in Crabtree negative yeast strains and respiratory pyruvate metabolism predominates. Elimination of pyruvate decarboxylase activity in Crabtree negative yeast strains appears to have no effect on aerobic growth on sugars. Examples of Crabtree negative yeasts can be found among *Candida utilis, Kluyveromyces marxianus*, and *Yarrowia lipolytica*.

"Threonine aldolase" (e.g., Glylp) refers to any protein (e.g., enzyme), which can catalyze the reaction converting threonine to the compounds acetaldehyde and glycine. "Lack of threonine aldolase activity" is defined as threonine aldolase activity in a strain that is below the detection limit of 0.005 micromoles minute$^{-1}$ mgprotein$^{-1}$ using methods previously described (24). "Reduced threonine aldolase activity" is defined as the activity exhibited by a particular yeast strain being less than the threonine aldolase activity of a parent yeast strain or its wild type strain that is grown under the same or similar conditions. "Overexpression of threonine aldolase," as used in the present invention refers to threonine aldolase activity of a particular yeast strain being greater than the activity observed in a wild type strain that is grown under the same or similar conditions.

The term "culture medium" refers to a solid or liquid medium comprising sufficient nutrients, including at least one carbon source, on which a microorganism (e.g., yeast) can grow. In chemostat or batch cultures the medium is a liquid.

"Culturing in a liquid medium" refers to growth of a microorganism and/or continued accumulation of lactic acid and pyruvic acid produced by a microorganism in a liquid culture medium.

"Carbon source" refers to an organic compound (e.g., glucose) or a mixture of organic compounds, which can be assimilated by a microorganism (e.g., yeast) and used to make new cell material.

"$C_2$ carbon source" refers to a carbon source having two carbons. Examples of $C_2$ carbon sources are acetate, acetaldehyde, and ethanol.

"Mineral media," "minimal media" or "synthetic media" refers to culture media for growing a microorganism (e.g., yeast) that comprises a nitrogen source, salts, trace elements, vitamins, and a carbon source, which are all defined. The carbon source can comprise at least one of glucose, sucrose, lactose, galactose, or fructose, among others. Synthetic media do not comprise for example, a nutrient source, whose composition is not defined, such as corn steep liquor, yeast extract or peptone, among others, which can be used in complex culture media. In certain embodiments, the mineral medium can comprise $(NH_4)_2SO_4$; $KH_2PO_4$; $MgSO_4$, EDTA, $ZnSO_4$, $CoCl_2$, $MnCl_2$, $CuSO_4$; $CaCl_2$; $FeSO_4$, $Na_2MoO_4$, $H_3BO_3$; KI, and optionally an antifoam agent.

"Capable of growing on a solid culture medium" refers to the ability of a microorganism (e.g., yeast) that has been streaked or spread on solidified culture medium so that colonies are not visible to the naked eye to produce at least one colony visible to the naked eye, after incubation in a suitable environment (e.g., pH and temperature among others) for a period of time.

"Capable of growing in a liquid culture medium" refers to the ability of a microorganism (e.g., yeast) that is introduced into a liquid culture medium under appropriate culture conditions (e.g., pH and temperature, among others) to replicate such that the biomass of the culture increases during the growth phase of the culture.

"Chemostat" refers to a device that allows for a continuous culture of microorganisms (e.g., yeast) in which both specific growth rate and cell number can be controlled independently. A continuous culture is essentially a flow system of constant volume to which medium is added continuously and from which continuous removal of any overflow can occur. Once such a system is in equilibrium, cell number and nutrient status remain constant, and the system is in a steady state. A chemostat allows control of both the population density and the specific growth rate of a culture through dilution rate and alteration of the concentration of a limiting nutrient, such as a carbon or nitrogen source.

It is known in the art that chemostats can be used in selection of mutants of microorganisms. By altering the conditions as a culture is grown in a chemostat (e.g., decreasing the concentration of a secondary carbon source necessary to the growth of the inoculum strain, among others) those microorganisms in the population that are capable of growing faster at the altered conditions will be selected and outgrow microorganisms that do not function as well under the new conditions. Typically such selection requires the progressive increase or decrease of at least one culture component over the course of growth of the chemostat culture.

"Batch culture" refers to either (a) a closed system of microorganisms with growth occurring in a fixed volume of culture medium that is continually being altered by the actions of the growing organisms until it is no longer suitable for growth, or (b) a system in which nutrients are fed to a culture of microorganisms without biomass being removed (e.g., as in the chemostat), wherein the microorganisms are altering their medium (e.g., environment). It is known in the art that extended cultivation of microorganisms in batch cultures (e.g., shake flasks) can be used to select for spontaneous mutants that grow relatively well under conditions in which the inoculum strain would not grow, or grows poorly.

"A series of batch cultures" involves growing a first batch culture of a first yeast strain in a culture medium with at least one defined component (i.e., the concentration of a particular carbon source) that is to be altered over the series. An aliquot of the first batch culture that has been grown is used to inoculate a second batch culture. An aliquot of the second batch culture that is grown is then used to inoculated a third culture, and so forth. The number of steps in a series can vary. Over the course of the series of batch cultures, the concentration of the defined component is increased or decreased. Those microorganisms that can grow best under the conditions at a given step (e.g., batch culture) in the series are selected (e.g., outgrowing other microorganisms that do not grow as well under the particular culture conditions) and used as inoculum for the next batch culture. Thus, over the course of the series, microorganisms that can grow under conditions that the first yeast strain cannot, or that grow better than the first yeast strain under the same growth conditions can be selected. It is known in the art to then isolate individual, pure strains from the culture that has been selected. This can be done by streak plating of a small amount of the cultured organisms, or by other methods known in the art.

"Selectable marker" refers to a nucleic acid sequence whose expression confers a phenotype facilitating identification of cells containing the nucleic acid sequence. Selectable markers include those, which confer resistance to toxic chemicals (e.g., ampicillin resistance, kanamycin resistance), complement a nutritional deficiency (e.g., uracil, histidine, leucine), or impart a visually distinguishing characteristic (e.g., color changes, fluorescence).

"Selection" refers to placing yeast under conditions that favor the growth of cells having a particular genotype or particular genotypes. The particular genotype (often the result of a genetic mutation) confers upon the selected yeast an advantage under certain environmental conditions so that the progeny of the selected yeast are able to outgrow and/or replace the parent.

The term "gene" refers to chromosomal DNA, plasmid DNA, cDNA, synthetic DNA, or other DNA that encodes a peptide, polypeptide, protein, or RNA molecule, and regions flanking the coding sequence involved in the regulation of expression.

"plasmid" refers to a circular, extrachromosomal, self-replicating piece of DNA.

"2 micron plasmid" refers to a yeast cloning vector that is capable of replicating within certain yeast cells (e.g., *S. cerevisiae*). Certain genes that can be located on the plasmid can be expressed when operably linked on the plasmid to a promoter recognized and used in the yeast host cell (e.g., yeast transformed with the 2 micron plasmid).

The term "genome" encompasses both the chromosome and plasmids within a host cell.

"Hybridization" refers to the ability of a strand of nucleic acid to join with a complementary strand via base pairing Hybridization occurs when complementary sequences in the two nucleic acid strands bind to one another.

"Mutation" refers to any change or alteration in a nucleic acid sequence. Several types exist, including point, frame shift, and splicing Mutation may be performed specifically or randomly.

"Open reading frame (ORF)" refers to a region of DNA or RNA encoding a peptide, polypeptide, or protein.

The term "promoter" or "promoter region" refers to a DNA sequence that includes elements controlling the production of messenger RNA (mRNA) by providing the recognition site for RNA polymerase and/or other factors necessary for start of transcription at the correct site.

"Transcription" refers to the process of producing a complementary RNA from a DNA template.

"Translation" refers to the production of protein from messenger RNA.

The term "yield" refers to the overall amount of pyruvic acid or a salt thereof produced (g/l) divided by the amount of glucose consumed (g/l) at the desired termination of a process for producing pyruvic acid or a salt thereof and the biomass catalyzing this conversion.

"Pyruvic acid" is defined as the sum of dissociated and undissociated forms of 2-oxopropanoic acid.

"At least a concentration of" refers to a minimum concentration (e.g., g pyruvic acid/l or mM) that can be reached in a particular yeast culture.

"Lactic acid" as used in the present invention encompasses both undissociated acid and lactic acid salts. Thus, X g lactic acid/100 g glucose refers to the total amount of undissociated lactic acid and lactate anion combined relative to each 100 g glucose fed to a fermentation. If a fermentation broth has a pH value between about 3.0 and 4.5, there will be a significant amount of lactic acid in the undissociated form. Indeed at a pH of 3.0 the molar ratio of undissociated lactic acid to lactate ion at 25° C. is about 7.0; and at a pH of about 4.5 the ratio at 25° C., is about 0.23. The total amount of undissociated lactic acid present in a solution is a function of both the pH of the solution and the overall concentration of lactic acid in the mixture. The lower the solution pH, the higher the percentage of the lactic acid that is present in its undissociated form. For example, where the medium is equal to the $pK_a$ of lactic acid (about 3.8), 50% of the lactic acid is present in the undissociated form. At pH 4.2, about 31% of the lactic acid is undissociated and at pH 4.0 and 3.9, about 41% and 47% respectively of the lactic acid is undissociated. The fraction of undissociated lactic acid is even lower at higher pH, 18% at pH 4.5 and 6.6% at pH 5.0.

"Fermentation broth" refers to a broth that is produced when a microorganism (e.g., yeast) is cultured in a liquid fermentation medium. The fermentation broth comprises any unused components of the liquid fermentation medium and any metabolites or products that result from fermentation by the organism.

"Oxygen limitation" or "limited oxygen supply" is defined as any condition in which oxygen transfer capacity from the gas to the liquid phase is lower than oxygen demands of a microorganism. This can be indicated by dissolved $O_2$ tension being close to zero, but can also occur at higher dissolved $O_2$ tension and depends on affinity of $O_2$ for the microorganism used.

It should be noted, that certain species names mentioned herein, such as *Torulopsis glabrata*, can refer to the name given in the species description by Barnet, Payne and Yarrow (1).

Certain embodiments of the present invention can be better understood with reference to FIG. 1. A Pdc negative strain 1 undergoes selection to recover a $C_2$ carbon source independent strain 2. The wild type of the Pdc negative strain is Crabtree positive. The Pdc negative yeast strain can be derived when pyruvate decarboxylase activity is eliminated in the wild type Crabtree positive yeast strain. The Pdc negative yeast strain can belong to a genus selected from the group consisting of *Saccharomyces, Candida, Schizosaccharomyces, Torulaspora, Kluyveromyces, Zygosaccharomyces* and *Dekkera* (also known as *Brettanomyces*, among other names known in the art). Preferably the Pdc negative yeast strain belongs to a genus selected from *Saccharomyces, Candida, Schizosaccharomyces*, and *Kluyveromyces*, more preferably *Saccharomyces*. In certain embodiments, the Pdc negative yeast strain belongs to a strain of *Kluyveromyces thermotolerans, Zygosaccharomyces bailii, Saccharomyces cerevisiae, Schizosaccharomyces pombe, Torulaspora globosa, Torulaspora delbruckii, Dekkera bruxellensis*, or *Candida glabrata* (also known as *Torulopsis glabrata*). Preferably the yeast strain belongs to *Saccharomyces cerevisiae* or *Candida glabrata*, more preferably the yeast strain belongs to *Saccharomyces cerevisiae*.

A Pdc negative yeast strain can comprise (A) at least one PDC structural gene that is capable of being expressed in the wild type yeast strain; (B) at least one PDC regulatory gene that is capable of being expressed in the wild type yeast strain; (C) a promoter of the PDC structural gene; and (D) a promoter of the PDC regulatory gene. In certain embodiments, at least one of (A)-(D) has been (i) mutated, (ii) disrupted, or (iii) deleted as part of producing a Pdc negative mutant. In certain embodiments, the Pdc negative yeast strain has all of the PDC structural genes that are capable of being expressed in the wild type yeast strain inactivated (e.g., by mutation, deletion, disruption, or use of antisense mRNA). A wild type PDC structural gene can for example, be interrupted using the loxP system, which is known in the art. A wild type PDC structural gene can also be disrupted by insertion of a selectable marker into the gene by homologous recombination. In still other embodiments, pyruvate decarboxylase activity can be eliminated from a wild type strain by using antisense RNA (e.g., method known in the art) to prevent translation of a PDC mRNA or a PDC regulatory gene's mRNA. Preferably the Pdc negative yeast strain belongs to *S. cerevisiae*, and the Pdc negative yeast strain has a genotype pdc1(−6, −2)::loxP pdc5 (−6,−2)::loxP pdc6(−6,−2)::loxP. In some embodiments the Pdc negative yeast is a *Saccharomyces cerevisiae* that has a genotype pdc1,5,6Δ (e.g., partial or complete deletion of the PDC 1, 5, 6 structural genes). In certain embodiments, the Pdc negative yeast strain 1 has no higher level of activity of threonine aldolase than in the wild type strain, when both are grown under essentially the same conditions. In some embodiments the Pdc negative yeast strain can be auxotrophic for ura, leu, or his, among others. In certain embodiments the Pdc negative yeast strain is ura−.

The selection for $C_2$ carbon source independent yeast strain 2 can involve growing a yeast culture in an aerobic carbon-limited chemostat. A first mineral medium is inoculated with a Pdc negative yeast strain 1. At the start of growing the culture in the chemostat, a first mineral medium that comprises glucose and a $C_2$ carbon source as the sole carbon sources and at concentrations sufficient to permit growth of the yeast culture can be used. The concentration of the $C_2$ carbon source in the first mineral medium is lowered during growth of the yeast culture in the chemostat until the concentration of the $C_2$ carbon source in the first mineral medium reaches a target range of between about 10% and 0% of total carbon, more preferably between about 5% and 0%, most preferably about 0%. The target range for the $C_2$ carbon source may vary for different strains of yeasts, as some may have different $C_2$ carbon source requirements for the growth of a Pdc negative strain. For example, a Pdc negative yeast strain might grow on 2% of total carbon, in which case the target range would be less than 2%, preferably 0%. In certain embodiments, in which the Pdc negative yeast strain 1 is auxotrophic (leu-, his-, and ura-, among others), the compound related to the auxotrophy needed for growth by the yeast is added to the medium in sufficient amount to allow growth of the culture. For example, if the yeast strain is ura minus, the first mineral medium can comprise uracil in sufficient amount to rescue the auxotrophy of the Pdc negative yeast strain 1.

After reaching the target range for the concentration of the $C_2$ carbon source in the first mineral medium during growth of the yeast culture in the chemostat at least one $C_2$ carbon source-independent yeast strain 2 can be recovered from the culture. The $C_2$ carbon source-independent yeast strain 2 preferably belongs to a genus or species as described above for the Pdc negative yeast strain 1. The $C_2$ carbon source-independent yeast strain 2 has no detectable amount of pyruvate decarboxylase activity. Preferably the lack of detectable activity is due to the mutations inherited from the Pdc negative parent strain. In certain embodiments, the $C_2$ carbon source-independent yeast 2 has no higher level of activity of threonine aldolase than in the wild type strain, when both are grown under essentially the same conditions. A $C_2$ carbon source-independent yeast 2 can be recovered using methods known in the art. For example, an aliquot from the culture when the $C_2$ carbon source is in the target range, can be spread on a solid culture medium comprising 2% ethanol as the sole carbon source. In some cases the aliquot may need to be diluted before being spread on a plate, as is known in the art. Using methods known in the art, individual colonies can then be isolated from the solid culture medium, after the yeast on the medium has been placed in an environment conducive to its growth. Cultures grown from individual colonies, should consist of yeast having a single genotype. An isolated yeast strain can also be tested to confirm that it is actually $C_2$ carbon source-independent. A $C_2$ carbon source-independent yeast strain 2 can also be tested to assure it has no detectable amount of pyruvate decarboxylase activity. In certain embodiments, the $C_2$ carbon source-independent yeast strain 2 does not grow well with relatively high concentrations (e.g., greater than about 5 mM) of glucose in mineral growth medium, and in some cases the strain 2 does not grow in mineral medium comprising even small amounts of glucose as the sole carbon source.

The $C_2$ carbon source-independent yeast strain 2 can, in some embodiments, be grown in a series of aerobic batch cultures using a second mineral medium to select a glucose tolerant $C_2$ carbon source-independent (GCSI) yeast strain 3. Glucose is the sole carbon source in the second mineral medium. Each successive batch culture is seeded with yeast grown in a batch culture from earlier in the series. The series of batch cultures is started with an amount of glucose present in the medium that permits growth of the $C_2$ carbon source-independent yeast strain 2. The $C_2$ carbon source-independent yeast strain that grows in the initial batch culture can be a mutant (e.g., GCSI strain) of the $C_2$ carbon source-independent yeast strain, the mutant can have the ability to grow with glucose as the sole carbon source (e.g., growth in the initial batch culture can be the result of a selection). The concentration of glucose is increased in the second mineral medium over the series of batch cultures. In certain embodiments, each successive batch culture begins with a higher concentration of glucose than the batch culture immediately preceding it. In other embodiments, the concentration is not increased in each and every batch culture over the series. For example, five consecutive batch cultures in the series might have the following glucose concentrations, 100 mM, 100 mM, 200 mM, 300 mM, and 400 mM. At least one GCSI yeast strain 3 can be recovered from the initial batch culture or from other batch cultures in the series of batch cultures. In certain embodiments, the GCSI yeast strain 3 can be isolated using the methods described above involving spreading an aliquot of a culture on a solid medium plate with glucose as the sole carbon source.

In certain embodiments, the $C_2$ carbon source-independent yeast strain 2 can be grown in a single aerobic batch culture using a second mineral medium comprising glucose as the sole carbon source to select a glucose tolerant $C_2$ carbon source-independent (GCSI) yeast strain 3. That is mutants of the $C_2$ carbon source-independent yeast strain 2 that can grow with glucose as the sole carbon source can be recovered as GCSI yeast strains 3 after being cultured in only a single batch culture (as opposed to a series of batch cultures).

Instead of using a series of batch cultures to select a GCSI yeast strain 3, in certain embodiments the $C_2$ carbon source-independent yeast strain 2 can be cultured in an aerobic chemostat in a second mineral medium. The chemostat can be the same as that used in the selection of the $C_2$ carbon source-independent yeast strain 2, or it can be a different chemostat. Glucose is the sole carbon source in the second mineral medium, and the concentration of glucose in the medium when starting the chemostat culture is such that it is growth-limiting for the $C_2$ carbon source-independent yeast strain 2. The concentration of glucose in the feed medium for the chemostat is gradually increased as the culture grows, such that another medium component becomes growth limiting and glucose is present in the culture in excess. At least one GCSI yeast strain 3 can be recovered from the chemostat, as described above for the series of batch cultures.

The GCSI yeast strain 3 is capable of growing with glucose as a sole carbon source, and the GCSI yeast strain 3 is more glucose tolerant than the recovered $C_2$ carbon source-independent yeast strain 2. Furthermore, the GCSI yeast strain 3 has no detectable amount of pyruvate decarboxylase activity. Preferably the lack of detectable activity is due to the mutations inherited from the Pdc negative strain. In certain embodiments, the GCSI yeast 3 has no higher level of activity of threonine aldolase than in the wild type strain, when both are grown under essentially the same conditions. The GCSI yeast strain 3 can be capable of growing in an aerobic batch culture and/or an aerobic chemostat. Still more, a GCSI yeast strain 3 can be capable of growing in a culture medium comprising at least one carbon source selected from the group consisting of glucose, sucrose, fructose, maltose, lactose, hydrolyzed starch, galactose, high fructose corn syrup, and lignocellulose hydrosulfate, preferably glucose.

Pyruvic acid or salts thereof can be produced by aerobically culturing a glucose tolerant $C_2$ carbon source-independent (GCSI) yeast strain 3 in a first culture medium. A wild type strain for the GCSI yeast strain 3 is Crabtree positive. Preferably the GCSI yeast strain 3 belongs to a genus or species as described above for the Pdc negative yeast strain. Preferably the GCSI yeast strain 3 belongs to *Saccharomyces cerevisiae* or *Candida glabrata*, more preferably the yeast belongs to *Saccharomyces cerevisiae*. The wild type strain of the GCSI yeast 3 is Crabtree positive.

The first culture medium that is used to culture the GCSI yeast strain 3 when producing pyruvic acid or a salt thereof 4 can comprise at least one carbon source selected from the group consisting of glucose, sucrose, fructose, maltose, galactose, lactose, hydrolyzed starch, high fructose corn syrup and hydrolyzed lignocelluloses. Preferably the first culture medium comprises at least one of sucrose or glucose; more preferably glucose is the sole carbon source in the medium. The first culture medium may also comprise compounds to overcome an auxotrophy of the GCSI yeast strain. The compounds used and the nature of the auxotrophy can vary for different yeasts. For example, if the yeast is *Saccharomyces cerevisiae* and it is ura-, uracil can be added to the medium to permit growth of the yeast. Alternatively, the ura—auxotrophy in the *Saccharomyces cerevisiae* can be overcome by introduction of a functional gene (e.g., URA3) into the yeast. For example, a gene (e.g., URA3) that can be expressed from a plasmid, can be introduced into the yeast by transformation or electroporation such that the auxotrophy is overcome. The first culture medium can be a mineral medium, in some embodiments. When the first culture medium is a mineral medium, it can comprise at least one carbon source selected from the group consisting of glucose, sucrose, fructose, maltose, galactose, and lactose, preferably sucrose or glucose, more preferably glucose.

In certain embodiments, the GCSI yeast strain 3 can be cultured in a mineral medium in an aerobic batch culture or in a chemostat under aerobic conditions, wherein the mineral medium comprises glucose as the sole carbon source. The mineral medium preferably comprises between about 1 mM and 1M glucose at the start of growing the batch culture, wherein glucose is the sole carbon source. In some embodiments, the batch culture medium can comprise between about 100 mM and 610 mM glucose, and in other embodiments the batch culture medium comprises between about 250 mM and 610 mM glucose.

When a GCSI yeast strain 3 is cultured to produce pyruvic acid or salts thereof 4, the culture can be grown in a batch culture, preferably a batch culture that is pH controlled. When the pH of a batch culture of a GCSI yeast strain 3 is controlled, it is preferably controlled between about 2.5 and 8, more preferably between about 3 and 6, and most preferably between about 4.5 and 5.5. Likewise, it is preferred that, when a GCSI yeast strain 3 is cultured in a chemostat for production of pyruvic acid or its salts, the pH of the culture in the chemostat is controlled, in a similar fashion (e.g., similar pH as for batch cultures).

In certain embodiments, when the GCSI yeast strain 3 is cultured in an aerobic batch culture in the first culture medium at least about 0.5 moles pyruvic acid 4 per liter can be produced, more preferably at least about 0.8 moles pyruvic acid 4 per liter can be produced, most preferably at least about 1.53 moles of pyruvic acid 4 per liter can be produced. When producing pyruvic acid 4 it is preferred that the culture have a pH of between about 4.8 and 5.2. The first culture medium can be a mineral medium. Some mineral mediums can comprise glucose as the sole carbon source. In certain embodiments the GCSI yeast strain 3 is capable of producing a yield of at least about 0.54 g pyruvic acid/g glucose, when cultured in an aerobic batch culture in a culture medium comprising at least glucose as a carbon source. In certain embodiments the GCSI yeast strain 3 is a *Candida glabrata*, and the GCSI yeast strain 3 is capable of producing greater than about 0.7 M pyruvic acid or a salt thereof 4 when cultured in mineral medium comprising a sugar (e.g., glucose) that can be used as a carbon source by the *Candida glabrata*.

Salts of pyruvic acids 4 that may be produced in the culture of the GCSI yeast strain include sodium pyruvate, potassium pyruvate, ammonium pyruvate, and calcium pyruvate. Preferably the salt, if present, is potassium pyruvate. More than one salt can be present in a given culture.

Pyruvic acids and/or salts thereof 4 can be purified 5 from the GCSI yeast strain 3 culture. Preferably biomass is removed from the fermentation broth. The biomass can be removed by methods known in the art. For example, the biomass can be removed by centrifugation or filtration, among others. Pyruvic acid or salts thereof 4 can be recovered and/or purified from a fermentation broth using methods known in the art. The fermentation broth can, for instance, be concentrated. In certain embodiments, a fermentation broth comprising pyruvic acid or its salts 4 can undergo an initial purification step that comprises precipitation and removal of certain impurities. Purification can also comprise acidification to obtain more free organic acid in the fermentation broth. Purification of a fermentation broth comprising pyruvic acid or its salts 4 can also involve careful separation of solids by filtration and, optionally, the separation of large solute molecular species by membrane filtration. Further, cations can be removed by a cation exchanger, and mineral acids can be removed by a conventional solid anion-exchanger. Thus, as discussed above, the fermentation broth can be purified using methods known in the art, and such methods can comprise at least one of distillation, ion exchange, nanofiltration or solvent extraction to produce purified pyruvic acid or salts thereof 5.

Certain embodiments of the present invention are directed to methods of selecting a glucose tolerant $C_2$ carbon source-independent (GCSI) yeast strain involving inoculating a Pdc negative yeast strain in a mineral medium. At the start of aerobically growing the culture, the first mineral medium comprises glucose and a $C_2$ carbon source as the sole carbon sources and at concentrations sufficient to permit growth of the yeast culture. Concentration of the $C_2$ carbon source in the first mineral medium is decreased during growth of the yeast culture, and concentration of the glucose is increased during growth of the yeast culture. In certain embodiments, the step of decreasing the concentration of the $C_2$ carbon source, and the step of increasing the concentration of glucose are performed simultaneously. Preferably both steps are performed in an aerobic chemostat. In other embodiments, the step of increasing the concentration of the glucose is performed before the step of decreasing the concentration of the $C_2$ carbon source. Preferably both steps are carried out in a single aerobic chemostat or alternatively the increasing step occurs in one aerobic chemostat and the decreasing step occurs in another aerobic chemostat. In still other embodiments, the step of decreasing the concentration of the $C_2$ carbon source is performed before the step of increasing the concentration of the glucose. Preferably the decreasing step is performed in an aerobic chemostat, while the increasing step is performed in the chemostat, another aerobic chemostat, a single batch culture, or over a series of batch cultures. The concentrations of carbon source and pH are as described above. After the increasing and decreasing steps are performed, a GCSI yeast strain can be recovered using methods known in the art. In certain embodiments a $C_2$ carbon source-independent yeast strain is not recovered as an intermediate step in the selection process. The recovered GCSI yeast strain is a described above.

Certain embodiments of the present invention are directed to GCSI yeast strains, as described above, that comprise a genome that comprises an exogenous lactate dehydrogenase gene (GCSI-L). The LDH is capable of being expressed in the GCSI yeast strain, and a protein resulting from the expression has lactate dehydrogenase activity. In some embodiments, the chromosome of the GCSI yeast strain comprises the exogenous lactate dehydrogenase gene. In some embodiments, the GCSI-L strain comprises at least one plasmid comprising the exogenous lactate dehydrogenase gene. In some embodiments, the plasmid can be a 2 micron plasmid. Preferably the exogenous lactate dehydrogenase gene is functionally linked to a promoter. In some embodiments the promoter can be selected from the group consisting of pyruvate decarboxylase promoters, alcohol dehydrogenase promoters, and L-threonine dehydrogenase promoters. Preferably the promoter is a triose phosphate isomerase promoter. In some embodiments the promoter can be a *Kluyveromyces* pyruvate decarboxylase promoter.

In some embodiments, the GCSI-L strain can be capable of producing lactic acid at a pH of about 5.0. The GCSI-L strain can be capable of producing lactic acid at a pH between about 5.0 and 2.67. The GCSI-L strain can be capable of producing greater than about 50 grams of lactic acid/100 grams glucose when cultured in a minimal medium comprising glucose as a sole carbon source. More preferably the GCSI-L strain can be capable of producing greater than about 60 grams of lactic acid/100 grams glucose when cultured in a minimal medium comprising glucose as a sole carbon source, and most preferably the GCSI-L strain can be capable of producing greater than about 70 grams of lactic acid/100 grams glucose.

In some embodiments, the GCSI-L strain belongs to a genus selected from the group consisting of *Saccharomyces, Candida, Schizosaccharomyces*, and *Kluyveromyces*. Preferably the GCSI-L yeast strain yeast strain is a *Saccharomyces cerevisiae*. In some embodiments the GCSI-L strain can be a *Saccharomyces cerevisiae* that has a genotype pdc1(-6,-2):: loxP pdc5(-6,-2)::loxP pdc6(-6,-2)::lox P ura3-52 YEpLpLDH. Certain embodiments are directed to a GCSI yeast strain that is a *S. cerevisiae* having a plasmid YEpLpLDH, wherein the GCSI yeast strain has a deposit number NRRL Y-30742.

YEpLpLDH is a yeast plasmid comprising the *Lactobacillus plantarum* LDH (see SEQ ID NO:3), and it is described in greater detail below. In some embodiments the exogenous LDH can be a *Lactobacillus plantarum*, bovine, *Lactobacillus casei, Bacillus megaterium, Rhizopus oryzae*, or *Bacillus stearothermophylus* lactate dehydrogenase gene. Examples of nucleotide sequences of such genes are available on Genbank under accession numbers AJ293008, NP 776524, M76708, M22305, Q9P4B6, and M19396, respectively. Preferably the exogenous lactate dehydrogenase gene is a *Lactobacillus plantarum* lactate dehydrogenase gene.

In certain embodiments, the GCSI-L strain can be capable of producing greater than about 60 $gl^{-1}$ lactic acid in a culture broth, when cultured aerobically or oxygen limited in a minimal medium. Preferably, the GCSI-L strain can be capable of producing greater than about 80 $gl^{-1}$ lactic acid in a culture broth, when cultured aerobically in a minimal medium, and more preferably the GCSI-L can be capable of producing greater than about 100 $gl^1$ lactic acid. In certain embodiments, the GCSI-L yeast strain is capable of producing lactic acid consisting essentially of L-lactic acid. In certain embodiments, the GCSI-L yeast strain can be capable of producing lactic acid when cultured under aerobic conditions in a minimal medium comprising glucose as a sole carbon source.

Certain embodiments of the present invention are directed to methods of producing lactic acid or salts thereof. The methods can involve aerobically culturing in a first culture medium a GCSI-L strain, wherein the GCSI yeast strain is capable of producing at least about 70 grams lactic acid/100 grams glucose when grown in a minimal medium comprising glucose as the sole carbon source. In certain embodiments, the culturing can be performed in an aerobic batch culture. In certain embodiments, the method can further comprise the step of recovering and purifying the lactic acid or a salt thereof. In some embodiments, the purification step can comprise at least one of distillation, ion exchange, nanofiltration or solvent extraction The following example is included to demonstrate preferred embodiments of the invention. It should be appreciated by those of skill in the art that the techniques disclosed in the example which follows represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Figure 2:
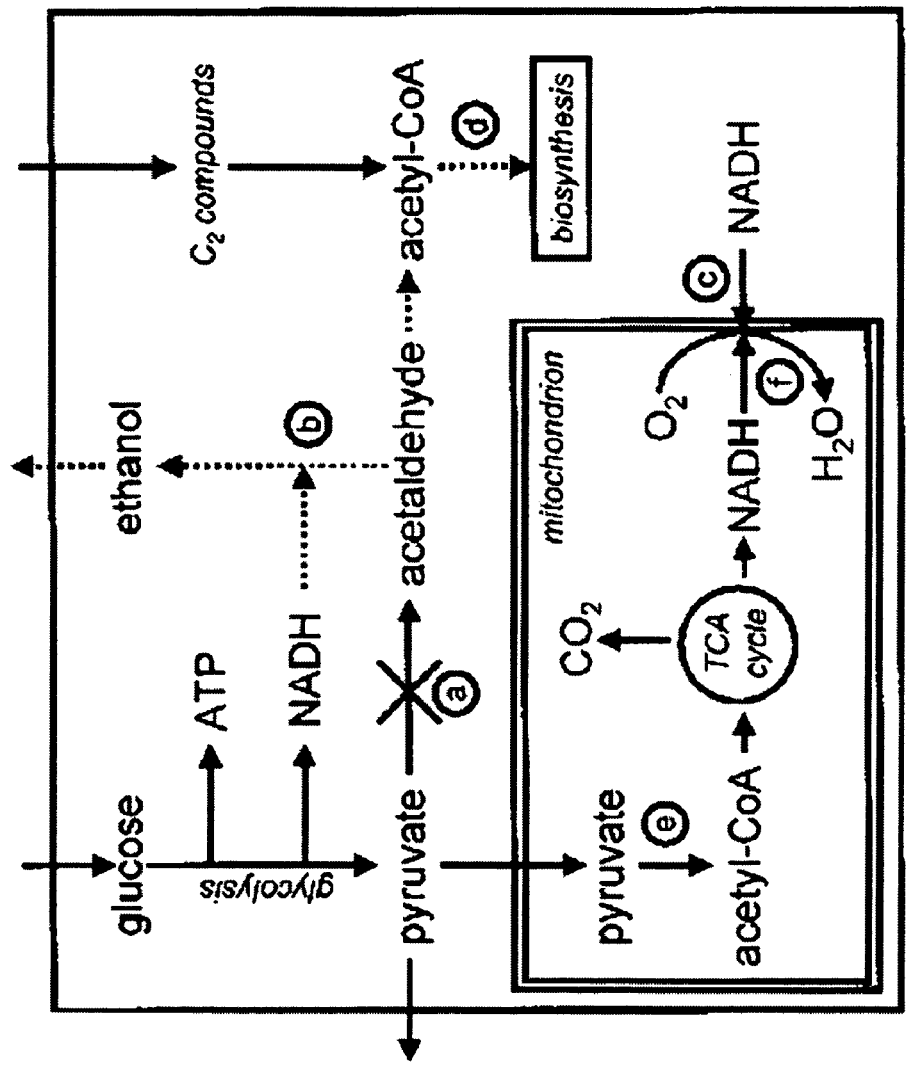
FIG. 2 is a schematic representation of the metabolism of Pdc negative *Saccharomyces cerevisiae* growing on glucose.

Two rounds of natural selection were used to obtain a *Saccharomyces cerevisiae* that has no detectable amount of pyruvate decarboxylase activity, that is $C_2$ carbon source-independent and that is glucose tolerant from a Pdc negative *Saccharomyces cerevisiae*. The nature of the Pdc negative strain can be better understood by referring to FIG. 2.

By the deletion of all genes encoding for pyruvate decarboxylase (reaction a) in *Saccharomyces cerevisiae*, two important processes (dotted lines) are impaired. First reoxidation of cytosolic NADH via alcohol dehydrogenase (reaction b) is blocked. Cytosolic NADH must therefore be oxidized by the mitochondria via external NADH dehydrogenase (reaction c) or via redox shuttle systems. Secondly the formation of cytosolic acetyl-CoA from acetaldehyde is blocked. Instead, the $C_2$ carbon source compounds required for the cytosolic acetyl-CoA for lysine and fatty-acid biosynthesis (reaction d) must be taken up from the environment. As oxygen consumption exceeds the oxygen necessary for oxidation of glucose to pyruvate, mitochondrial oxidation of pyruvate, via pyruvate dehydrogenase (reaction e) and the tricarboxylic acid cycle (TCA cycle) occurs, resulting in $CO_2$ formation and the oxidation of NADH via internal NADH dehydrogenase (reaction f).

An acetate independent mutant derived from a Pdc negative strain was obtained via carbon-limited (e.g., glucose and acetate were the sole carbon sources) aerobic chemostat cultivation by progressively lowering the acetate in the feed. Further selection for glucose tolerance in aerobic shake flasks resulted in a *Saccharomyces cerevisiae* mutant (TAM) that can grow in aerobic batch cultures on synthetic medium with glucose as the sole carbon source and that does not have pyruvate decarboxylase activity or threonine aldolase overexpression. Physiological characterization of the TAM strain revealed a strong tendency for pyruvate production. In pH controlled batch culture a concentration of 135 g/l pyruvate (pyruvate calculated using the molecular weight of pyruvic acid) can be obtained with a specific pyruvate production rate of about 6-7 mmol (g biomass)$^{-1}$ h$^{-1}$ during the exponential growth phase and an overall yield of up to about 0.54 g pyruvate/g glucose.

Strains and maintenance. All *Saccharomyces cerevisiae* strains used in the Example (Table 1) were derived from the congenic CEN.PK family (19). Stock cultures were prepared from shake flask or chemostat cultures, by addition of 20% (v/v) glycerol to cultures and storage of 2 ml aliquots in sterile vials at −80° C. All selected strains were routinely checked for uracil auxotrophy as a negative control for strain identity.

TABLE 1

*Saccharomyces cerevisiae* strains used

| Strain | Description |
| --- | --- |
| CEN.PK 113.7D | MATa URA3 PDC1 PDC5 PDC6 Wild type yeast having pyruvate decarboxylase activity |
| CEN.PK182 | MATa pdc1(−6, −2)::loxP pdc5(−6, −2)::loxP pdc6 (−6, −2)::loxP Pdc negative yeast |
| CEN.PK111-61A | MATa ura3-52 1eu2-112 his3-Al ura⁻ yeast |
| RWB837 | MATa pdc1(−6, −2)::loxP pdc5(−6, −2)::loxP pdc6(−6, −2)::loxP ura3-52 Pdc negative ura⁻ yeast |
| RWB837* | "MATa pdc1(−6, −2)::loxP pdc5(−6, −2)::loxP pdc6 (−6, −2)::loxP ura3-52"ura− yeast having no pyruvate decarboxylase activity, $C_2$ carbon source independent, glucose intolerant |
| TAM | "MATa pdc1(−6, −2)::loxP pdc5(−6, −2)::loxP pdc6(−6, −2)::loxP ura3-52"ura− yeast having no pyruvate decarboxylase activity, $C_2$ carbon source independent, glucose tolerant |

Note that none of the strains overexpress threonine aldolase.

Strain construction. RWB837 was obtained from a cross between CEN.PK182 and CEN.PK111-61A (both provided by Dr. P. Kotter, Frankfurt, Germany). The resulting diploid was sporulated and the spores were heated for 15 minutes at 56° C. The mix was then plated on YP (yeast peptone medium) with 0.2% acetate as the carbon source. The resulting colonies were tested for growth on YP medium with glucose or ethanol. Colonies that could not grow on glucose were subsequently checked by PCR for the presence of a disrupted PDC6 gene and the mating type. Determination of the auxotrophic markers present, in this case ura3-52, then gave RWB837. The final (TAM) strain, selected as described below, was transformed with YEplac195 (8) according to the high-efficiency protocol described by Gietz and Woods (9), resulting in the prototrophic (ura⁺) TAM+YEplac195 strain.

In one aspect, the invention discloses and claims fungal host cells and cell cultures comprising glucose tolerance and $C_2$ carbon source independence as disclosed herein, and in particular, cells of *Saccharomyces cerevisiae* strains, which comprise RWB837 and its derivatives including TAM, particularly those that are $C_2$ carbon source independent, or both carbon source independent and glucose tolerant (e.g., TAM).

Such cells and cell cultures may be substantially biologically-pure cultures that comprise, consist essentially of, or consist of a single strain. Illustrative embodiments of the present invention, in the form of biologically-pure cultures of strains RWB837 (MATa pdc1(−6,−2)::loxP pdc5(−6,−2):: loxP pdc6(−6,−2)::loxP ura3-52), RWB837* ("MATa pdc1(− 6,−2)::loxP pdc5(−6,−2)::loxP pdc6(−6,−2)::loxP ura3-52" ura-yeast having no pyruvate decarboxylase activity, $C_2$ carbon source independent, glucose intolerant), and TAM ("MATa pdc1(−6,−2)::loxP pdc5(−6,−2)::loxP pdc6(−6,−2):: loxP ura3-52" ura-yeast having no pyruvate decarboxylase activity, $C_2$ carbon source independent, glucose tolerant) have been deposited under conditions that assure that access to the cultures will be available during the pendency of this patent application to one determined by the Commissioner of Patents and Trademarks to be entitled thereto under 37 C. F. R. § 1.14 and 35 U.S.C. §122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the finishing of a sample of the deposit, and in any case, for a period of at least 30 (thirty) years after the date of deposit or for the enforceable life of any patent which may issue disclosing the cultures. The depositor acknowledges the duty to replace the deposits should the depository be unable to furnish a sample when requested, due to the condition of the deposits. All restrictions on the availability to the public of the subject culture deposits will be irrevocably removed upon the granting of a patent disclosing them.

Cultures CEN.PK113.7D, CEN.PK 182, CEN.PK 111-61A, RWB837, RWB837*, and TAM were deposited in the permanent collection of the Northern Regional Research Center (NRRL), Agricultural Research Service Culture Collection, National Center for Agricultural Utilization Research, US Department of Agriculture, 1815 North University Street, Peoria, Ill. 61604, U.S.A. on Apr. 29, 2003 under the terms of the Budapest Treaty, and accorded the accession numbers NRRL Y-30646, NRRL Y-30647, NRRL Y-30648, NRRL Y-30649, NRRL Y-30650, and NRRL Y-30651, respectively.

Chemostat cultivation. Aerobic carbon-limited or nitrogen-limited chemostat cultivations were performed as described previously (23). To rescue auxotrophy, uracil (15) was added to the media. The synthetic medium for the glucose-limited chemostat cultures contained 250 mM substrate carbon. When acetate was present, this was added on top of the 250 mM carbon from glucose, ranging from 0-5% acetate on substrate carbon basis. For nitrogen-limited cultures the glucose concentration in the synthetic medium was adjusted such that a residual glucose concentration in the culture broth of approximately 100 mM was obtained.

Shake flask cultivation. The 500 ml shake flasks, containing 100 ml synthetic medium (27) were incubated at 30° C. in a rotary shaker (200 rpm). To rescue auxotrophy 0.15 gl$^{-1}$ uracil (15) was added to the media. Precultures of RWB 837 were grown on 2% ethanol. For all other shake-flask cultures glucose was used as the carbon source, with concentrations ranging from 2 to 10%. The selected strain was routinely checked for uracil auxotrophy to indicate culture purity.

Fermenter batch cultivation. Aerobic batch cultivation was performed at 30° C. in 2L fermenters (Applikon, Schiedam, the Netherlands) with a working volume of 1 liter. The pH was controlled at 5.0 via automated addition of 10 M KOH (Applikon ADI 1030 biocontroller). The dissolved oxygen concentration was maintained above 10% of air saturation at all times by adjusting the stirrer speed between 800-1000 rpm and the air flow between 0.50-0.75 1 $\text{min}^{-1}$. A synthetic medium with double the concentrations as described by Verduyn et al. (27) was used. The initial glucose concentration was 100 $\text{gl}^{-1}$. During the repeated batch 100 g of non-sterile solid glucose was added twice at 32 and 48 h after inoculation. Antifoam (BDH) was added to the fermenters when required. Culture purity was checked by microscope at the end of the fermentation and no contaminants were observed.

Microarray analysis. Sampling of cells from chemostats, probe preparation and hybridization to Affymetrix GeneChip® Microarrays was performed as described previously (14). The results were derived from two independently cultured replicates for the selected Pdc negative strain and from three independently cultured replicates for the wild type.

Micro array data acquisition and analysis. Acquisition and quantification of array images and data filtering were performed using the Affymetrix software packages: Microarray Suite v5.0, MicroDB v3.0 and Data MiningTool v3.0. For further statistical analyses Microsoft Excel running the Significance Analysis of Microarrays (SAM; v1.12) add-in was used, with a delta value that corresponded with the minimum expected median false-positive rate and a minimum change of 2-fold (18). In our experience, these criteria establish a data set able to be reproduced by an independent laboratory (14).

Before comparison, all arrays were globally scaled to a target value of 150 using the average signal from all gene features using Microarray Suite v5.0. From the 9,335 transcript features on the YG-S98 arrays a filter was applied to extract 6,383 yeast open reading frames of which there were 6,084 different genes. This discrepancy was due to several genes being represented more than once when sub-optimal probe sets were used in the array design. Since the lowest 900 transcripts could not be reliably measured, their level was set to a value of 12 for the comparison analyses.

Promoter analyses were performed using the web-based software "Regulatory Sequence Analysis Tools" (20) as was described previously (2).

Analytical procedures. Dry weight determination, glucose, acetate and metabolite analysis, gas analysis and pyruvate decarboxylase and threonine aldolase assays were performed as described previously (24). The protein content of whole cells was determined by a modified burette method (25).

Results

Selection of $C_2$ carbon source-independent *Saccharomyces cerevisiae* from Pdc negative *Saccharomyces cerevisiae* in chemostat cultures. In this study, the power of chemostat cultivation as a tool for the selection of microorganisms (3,10), was used in an attempt to eliminate the $C_2$-carbon source requirement of Pdc negative *Saccharomyces cerevisiae* (4,5). For the selection apdc1,5,6Δ ura3 Δ*Saccharomyces cerevisiae* strain (RWB 837) was used. The ura3 Δ auxotrophic marker was used as a control for culture purity. First, a steady state of Pdc negative *Saccharomyces cerevisiae* on a mixture of 5% acetate and 95% glucose on carbon basis was obtained. The metabolism of this culture was fully respiratory, as was indicated by a respiratory quotient of one carbon dioxide produced per oxygen consumed, the biomass yield on carbon was 14.6 g biomass $\text{Cmol}^{-1}$ and all glucose and acetate was consumed. Then the acetate content of the synthetic medium was lowered in 5 consecutive steps from 5% of the total carbon content to zero. Each step lasted 5 volume changes. During this slow transition, RWB 837 adapted for growth in aerobic carbon-limited chemostat cultures, with glucose as the sole carbon source, at a dilution rate of 0.10 $\text{h}^{-1}$. The biomass yield (14.7 g biomass $\text{Cmol}^{-1}$), oxygen consumption rate and carbon dioxide production rate (both 2.9 mmol $\text{gbiomass}^{-1}$ $\text{h}^{-1}$) of this glucose-limited culture indicated fully respiratory metabolism of the $C_2$ carbon source-independent (e.g., lacking pyruvate decarboxylase activity and lacking ethanol production) *Saccharomyces cerevisiae* strain, equal to that of wild type *Saccharomyces cerevisiae* under these conditions (21).

Transcriptome analysis of the $C_2$ carbon source-independent Pdc negative *Saccharomyces cerevisiae* strain. Transcriptome analysis of the glucose-limited chemostat culture of the $C_2$ carbon source-independent *Saccharomyces cerevisiae* strain was performed. The $C_2$ carbon source-independent Pdc negative strain was compared with glucose-limited chemostat cultures of the wild type (14). Of the genes with a known function, only 18 were upregulated and only 16 genes were downregulated in the selected strain. These upregulated genes included 11 genes involved in meiosis or sporulation (HOP2, IME2, REC102, REC1O4, RED1, SLZ1, SPOI3, SPOI6, SPRI, YER179 and ZIP1). The other seven upregulated genes were CAR1, ECM1, HXT3, HXT4, IRE1, NUF1 and NUF2. The downregulated genes included four highly predictable genes (PDC1, PDC5, PDC6 and URA3) and in addition ALP1, AQY1, GND2, FU11, HSP30, HXT5, MEP2, MLS1, PDRI2, PHO4, SSA3. SSA4, among others. Expression of GLY1, the gene that when overexpressed can rescue the $C_2$ carbon source auxotrophy of Pdc negative *Saccharomyces cerevisiae*, was not significantly changed in the selected strain.

Figure 3:
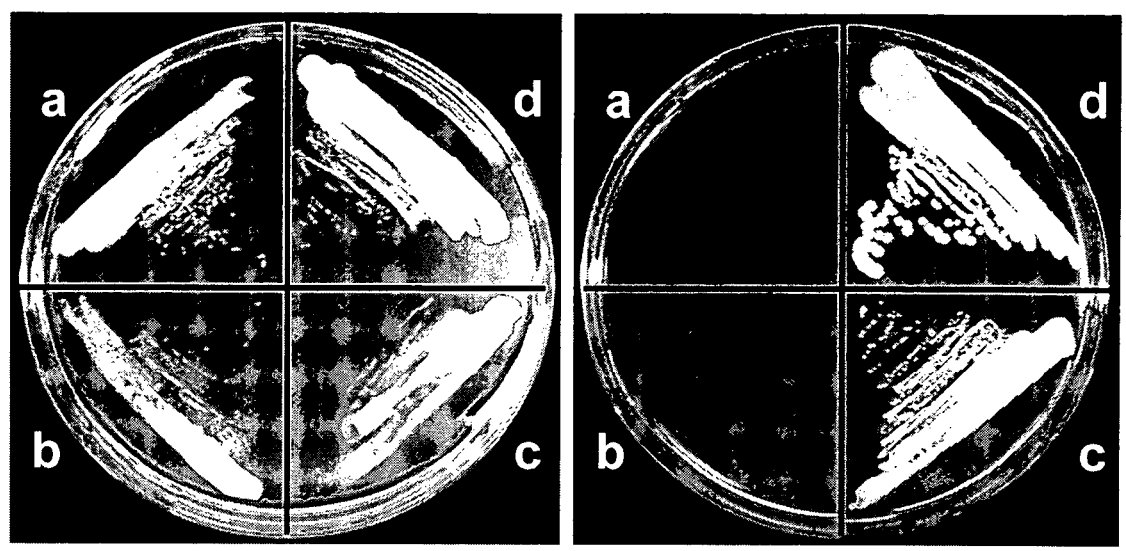
FIG. 3 shows the growth of (a) a *Saccharomyces cerevisiae* Pdc negative strain, (b) a *Saccharomyces cerevisiae* $C_2$ carbon source-independent strain lacking pyruvate decarboxylase activity, (c) a *Saccharomyces cerevisiae* glucose tolerant strain of the present invention that lacks pyruvate decarboxylase activity and is also $C_2$ carbon source-independent (e.g., GCSI yeast), and (d) wild type (e.g., having pyruvate decarboxylase activity) *Saccharomyces cerevisiae* on synthetic-medium agar plates with ethanol (left plate) or glucose (right plate) as the sole carbon source.

Selection for glucose tolerance in shake flask cultures. After the selection for $C_2$ carbon source-independence, a small aliquot of the chemostat culture was transferred to a shake flask with synthetic medium containing uracil and 20 $\text{gl}^{-1}$ glucose. As was expected from previous results, both the original Pdc negative *Saccharomyces cerevisiae* and the $C_2$-independent strain did not grow on agar plates with synthetic medium, uracil and glucose, whereas both strains did grow on agar plates with synthetic medium, uracil and ethanol (FIG. 3).

In agreement with this, no growth was observed during the first seven days of the initial shake flask culture of the $C_2$ carbon source-independent strain on glucose. Prolonged cultivation of the $C_2$ carbon source-independent strain, however, resulted in significant biomass formation, indicating an accumulation of spontaneous glucose-tolerant mutants. The observed specific growth rate was well below 0.01 $\text{h}^{-1}$. After growth had ceased, which occurred at relatively low biomass density due to acidification of the culture by pyruvic acid excretion, one ml of the culture was transferred to a next 500 ml shake flask containing 100 ml identical synthetic medium.

The process of serial transfer was repeated 27 times in total. The specific growth rate of the Pdc negative strain in the sixth shake flask was already 0.10 $\text{h}^{-1}$ on 20 $\text{gl}^{-1}$ glucose. After 14 shake flask cultivations and an obtained specific growth rate of 0.18 $\text{h}^{-1}$, the glucose content of the medium was raised to 32, 54, 69 and 100 $\text{gl}^{-1}$ in consecutive cultures. At this high concentration of glucose the obtained $C_2$ carbon source-independent and glucose-tolerant Pdc negative *Sac-* charomyces cerevisiae strain grew at a specific growth rate of 0.20 h$^{-1}$ in shake flasks on glucose as the sole carbon source.

The culture, possibly existing of a mixture of different spontaneous mutants, was streaked on agar plates with synthetic medium, glucose and uracil. Four of the resulting colonies were tested for growth in shake flasks on glucose and no significant differences in specific growth rate were observed. One of these cultures was chosen for further study and this C$_2$ carbon source-independent glucose tolerant Pdc negative Saccharomyces cerevisiae strain will be designated as TAM in the following discussion.

The differences in growth between the original Pdc negative (RWB 837), the C$_2$ carbon source-independent yeast strain, the TAM strain and the wild type, on synthetic medium with glucose or ethanol as the sole carbon source were clearly demonstrated by agar-plate growth as depicted in FIG. 3.

In FIG. 3, both plates are supplemented with uracil to rescue the auxotrophy of the Pdc negative Saccharomyces cerevisiae strains. Ethanol plates were incubated for incubated for 7 days, whereas glucose plates were incubated for 3 days. The strains used were: a. RWB837 (Pdc negative Saccharomyces cerevisiae), b. RWB837* (selected C$_2$ carbon source-independent Saccharomyces cerevisiae), c. TAM (selected C$_2$ carbon source-independent and glucose-tolerant Saccharomyces cerevisiae), d. CEN.PK 113-7D (wild type) on synthetic-medium agar plates with ethanol (left plate) or glucose (right plate) as the sole carbon source.

Although the TAM strain displayed a three-day-longer lag phase, all four strains grew on plates with ethanol as a carbon source. As described above, when glucose was the carbon source the original Pdc negative strain (RWB837) and the C$_2$ carbon source-independent strain did not grow. Consistent with the growth in shake flasks on glucose, the selected TAM strain, and of course the wild type, proliferate well on the agar-plates with glucose (FIG. 3).

Pyruvate Production by the Selected TAM Strain in Fermenter Cultures.

Figure 4:
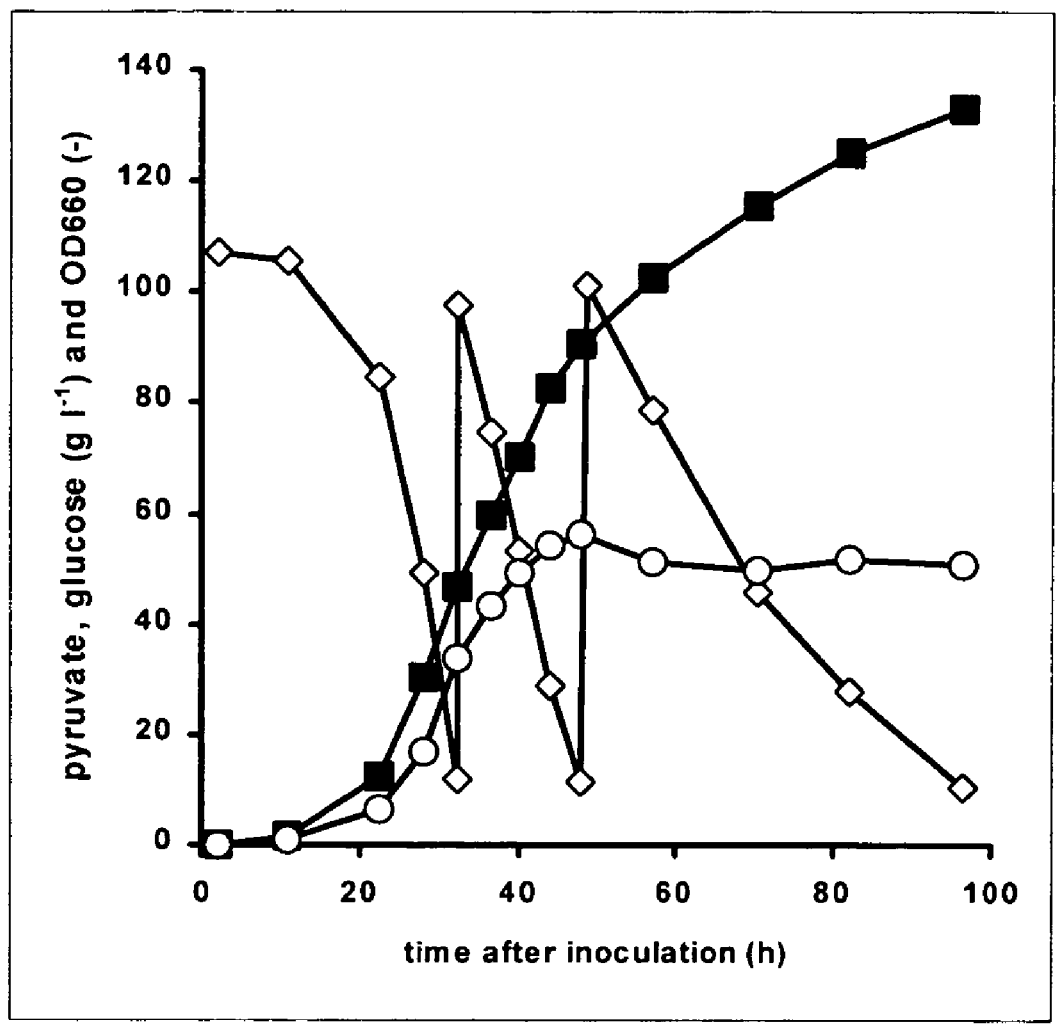
FIG. 4 is a graph depicting growth and pyruvate production during an aerobic repeated batch culture on glucose of a GCSI *Saccharomyces cerevisiae* (e.g., the selected TAM strain of the present invention). The results shown are from one representative batch experiment. Replicate experiments yielded essentially the same results. The closed squares refer to the pyruvate concentration. The open symbols refer to the glucose concentration (diamonds) or OD660 (circles).

During the selection for glucose tolerance in shake flasks a rapid acidification of the culture due to pyruvate excretion was observed. To further assess the potential of the TAM strain for the production of pyruvate the fermentation was continued as a repeated batch by the addition of solid glucose to the fermenter (FIG. 4). Aerobic batch cultivations on 100 gliter$^{-1}$ initial glucose were performed in fermenters at constant pH. During this repeated batch phase the specific growth rate gradually decreased until growth ceased, probably due to nutrient limitations in the medium. During the exponential growth phase (FIG. 4) the maximum specific growth rate of the TAM strain was 0.20 h$^{-1}$, which equaled the maximum specific growth rate in shake flasks. Consistent with the observations in shake flasks, large amounts of pyruvate were produced in fermenter cultures. The pyruvate concentration in the supernatant exceeded 100 gl$^{-1}$ within 60 hours after inoculation of the fermenter. The rate of pyruvate production during the exponential growth phase was 6-7 mmol gbiomass$^{-1}$ h$^{-1}$. In the first 40 h of this batch, starting with a low biomass concentration (an OD660 of 0.1), a pyruvate concentration of 50 gl$^{-1}$ was obtained with a yield of 0.55 g pyruvate g glucose$^{-1}$. The final concentration of pyruvate acid obtained after 100 hours was 135 gl$^1$, with an overall yield of 0.54 g pyruvate g glucose$^{-1}$.

Glucose-limited chemostat cultivation of the TAM strain. The obtained maximum specific growth rate of the TAM strain in batch on glucose was 0.20 h$^{-1}$. Under the same conditions wild type Saccharomyces cerevisiae CEN.PK 113-7D grew with a higher maximum specific growth rate of 0.37 h$^{-1}$ (data not shown). To further study this deviation in growth, glucose-limited chemostat cultures of the TAM strain were performed at increasing dilution rates. The TAM strain fully respired the consumed glucose to carbon dioxide and water at a dilution rate of 0.10 h$^{-1}$. Taking the lower yield of the selected strain (0.43 g biomass g glucose$^{-1}$) compared to the wild type (0.48 g biomass g glucose$^{-1}$) into account, the other physiological parameters were comparable to the wild type as described by van Hoek et alt. (21) At a dilution rate of 0.15 h$^{-1}$ the biomass yield of the TAM strain had increased to 0.47 g biomass g glucose$^{-1}$, which is still lower than the 0.50 g biomass g glucose$^{-1}$ for the wild type at this dilution rate. The TAM strain was capable of growth at a dilution rate of 0.20 h$^{-1}$ in glucose limited chemostat cultures, but this growth was accompanied by a highly variable pyruvate production (0.25-0.45 mmol pyruvate gbiomass$^{-1}$ h$^{-1}$). At a dilution rate of 0.23 h$^{-1}$ the TAM strain washed out of the chemostats, indicating a maximum specific growth rate of this strain between 0.20 h$^{-1}$ and 0.23 h$^{-1}$ in glucose-limited chemostat cultures. After this prolonged glucose-limited chemostat cultivation an aliquot of the culture was transferred to a shake-flask with 100 gl$^{-1}$ of glucose. In this shake flask rapid growth was observed, indicating that the culture had maintained the glucose-tolerant phenotype.

Nitrogen-limited chemostat cultivation of the TAM strain. Comparison of the selected TAM strain with wild type Saccharomyces cerevisiae CEN.PK 113-7D is most adequate at high glucose concentrations and in the absence of C$_2$-compounds in the medium. Nitrogen-limited chemostat cultivation at the same dilution rate with glucose as the sole carbon source, combines these conditions with the advantages of chemostat cultivation in quantitative physiological studies. The glucose concentrations in the synthetic medium were chosen such that approximately the same residual glucose concentration was obtained in the cultivations of both strains (Table 2).

Table 2 summarizes properties of the TAM (GCSI Saccharomyces cerevisiae) strain and the isogenic wild type CEN.PK 113-7D in aerobic nitrogen-limited chemostat culture at a dilution rate of 0.10 h$^{-1}$. The wild type data are obtained from the same cultures as used by Boer et al. (2003) (2). Averages and mean deviations were obtained from duplicate (TAM) and triplicate (wild type) experiments, respectively, with independent steady-state cultures. Calculations of the carbon recovery were based on a carbon content of biomass of 48% (w/w) and include the residual glucose concentrations in the broth. $Y_{SX}$, $Y_{NX}$ and $Y_{ATP}$ are the biomass yields on glucose, nitrogen and ATP. The $Y_{ATP}$ was calculated according to Verduyn (1992) (27), assuming a fixed P/O-ratio of 1.

TABLE 2

|  | Wild type | TAM |
|---|---|---|
| Reservoir glucose concentration (g · l$^{-1}$) | 58.8 ± 0.1 | 35.1 ± 0.1 |
| Residual glucose concentration (g · l$^{-1}$) | 16.7 ± 0.7 | 20.4 ± 0.1 |
| $Y_{sx}$ (g$_{biomass}$ · g$_{glucose}^{-1}$) | 0.09 ± 0.00 | 0.21 ± 0.00 |
| $Y_{nx}$ (g$_{biomass}$ · g$_N^{-1}$) | 18.8 ± 0.1 | 14.7 ± 0.1 |
| $Y_{ATP}$ (g$_{biomass}$ · mol$_{ATP}^{-1}$) | 6.8 | 8.3 |
| Protein content (g$_{protein}$ · g$_{biomass}^{-1}$) | 0.29 ± 0.01 | 0.33 ± 0.01 |
| RQ | 4.5 ± 0.2 | 0.70 ± 0.01 |
| q$_{glucose}$ (mmol · g$_{biomass}^{-1}$ · h$^{-1}$) | 5.8 ± 0.1 | 2.6 ± 0.1 |
| q$_{ethanol}$ (mmol · g$_{biomass}^{-1}$ · h$^{-1}$) | 8.0 ± 0.1 | <0.01 |
| q$_{pyruvate}$ (mmol · g$_{biomass}^{-1}$ · h$^{-1}$) | 0.1 ± 0.0 | 2.8 ± 0.0 |
| q$_{glycerol}$ (mmol · g$_{biomass}^{-1}$ · h$^{-1}$) | 0.08 ± 0.00 | <0.01 |
| q$_{acetate}$ (mmol · g$_{biomass}^{-1}$ · h$^{-1}$) | 0.06 ± 0.02 | <0.01 |
| q$_{CO2}$ (mmol · g$_{biomass}^{-1}$ · h$^{-1}$) | 12.1 ± 0.2 | 2.8 ± 0.0 |

TABLE 2-continued

|  | Wild type | TAM |
|---|---|---|
| $q_{O2}$ (mmol · $g_{biomass}^{-1}$ · $h^{-1}$) | 2.7 ± 0.1 | 4.0 ± 0.1 |
| Consumed carbon recovery (%) | 94.0 ± 1.0 | 97.4 ± 0.7 |
| Total carbon recovery (%) | 95.6 ± 0.7 | 98.6 ± 0.4 |

The wild type showed alcoholic fermentation, as is characteristic for *Saccharomyces cerevisiae* under glucose-excess conditions. This resulted in a low biomass yield on glucose (0.09 g biomass g glucose$^{-1}$), an ethanol production rate of 8.0 mmol gbiomass$^{-1}$ h$^{-1}$ and a respiratory quotient of 4.5 mmol carbon dioxide produced mmol oxygen consumed$^{-1}$. The protein content (0.29 g protein g biomass$^{-1}$) and the biomass yield on nitrogen (18.8 g biomass g nitrogen$^{-1}$) are in good agreement with previously published values (22,23) for nitrogen-limited chemostat cultures of the wild type.

Under the same conditions, the TAM strain that fully depends on respiration in the absence of alcoholic fermentation had a higher biomass yield on glucose (0.21 g biomass g glucose$^{-1}$) and produced pyruvate as the only by-product at a rate of 2.8 mmol gbiomass$^{-1}$ h$^{-1}$ (Table 2). The oxygen consumption rate was 4.0 mmol g biomass$^{-1}$ h$^{-1}$ compared to 2.7 mmol g biomass$^{-1}$ h$^{-1}$ for the wild type. The respiratory oxidation of the NADH formed during pyruvate formation lowered the respiratory quotient to 0.70 mmol carbon dioxide produced per mmol oxygen consumed. The protein content of the biomass was slightly higher for the TAM strain (0.33 g protein g biomass$^{-1}$) than it was for the wild type (0.29 g protein g biomass$^{-1}$). This higher protein content of the cells partially explains the significantly lower yield on nitrogen of the TAM strain (14.7 g biomass g nitrogen$^{-1}$) compared to the wild type (18.8 g biomass g nitrogen$^{-1}$).

Transcriptome analysis of the TAM strain. Central in transcriptome analysis is the choice of the adequate culture conditions for comparison. In the case of the selected TAM strain the absence of $C_2$-compounds and the presence of high levels of glucose in the broth are typical for uncovering its phenotype. To combine the benefit of chemostat cultures in microarray studies (14) and the requirement for glucose excess, the nitrogen-limited chemostat cultures of the TAM strain and the isogenic wild type CEN.PK 113-7D, were chosen for the transcriptome analysis.

The comparison of the nitrogen-limited chemostat cultures revealed 305 genes of which the mRNA level was at least two-fold higher in the TAM strain than in the wild type. The mRNA abundance of 168 genes was at least two-fold lower in the TAM strain than in the wild type. In total the genes with at least two-fold changed mRNA levels comprise almost 8% of the total *Saccharomyces cerevisiae* genome. Of these changed genes, 273 (58%) have an unknown function, which is higher than the percentage of not fully annotated genes in the whole *Saccharomyces cerevisiae* genome (47%).

Sequence analysis of the upstream regions of genes upregulated in the selected strain showed an overrepresentation of possible Mig binding sites amongst these genes. Although the transcript level of the primarily posttranscriptionally (7) regulated MIG1 is not changed, the transcript level of its close homologue MIG2 was almost 11-fold downregulated. Many genes, required for growth on other carbon sources than glucose, were upregulated in the TAM strain. This included genes involved in gluconeogenesis and ethanol utilization (ACS1, ADH2, ADR1, CAT8, FBP1, SIP4), fatty acid metabolism (CAT2, CRC1, ECI1, FAA2, FOX2, PEX11, POT1, POT1, YAT2), galactose metabolism (GAL2, GAL3, GAL4), maltose metabolism (YDL247W, YFL052W, YJRI60C) and pyruvate and lactate metabolism (DLD1, JEN1).

Figure 5:
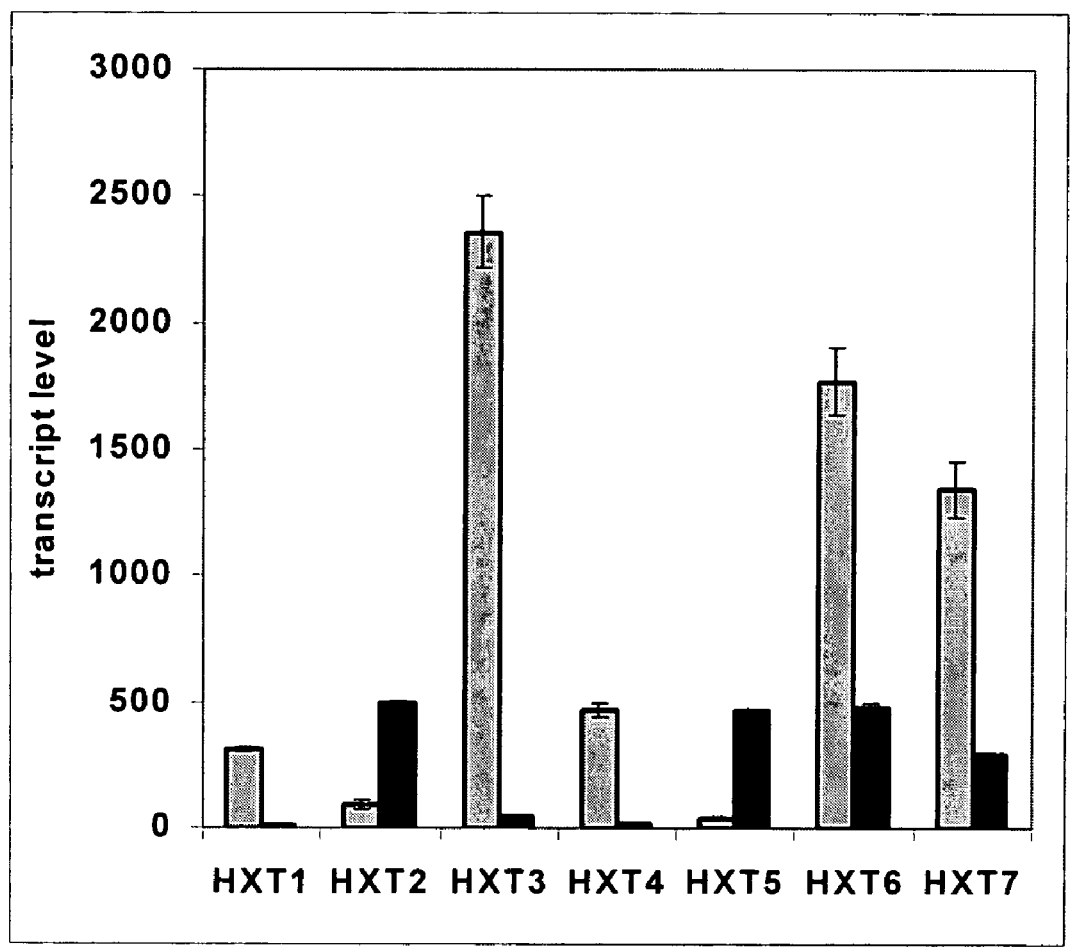
FIG. 5 is a transcript-level comparison of the main hexose transporters (HXT1-7), between a GCSI *Saccharomyces cerevisiae* of the present invention and its isogenic wild type in nitrogen-limited chemostat cultures with glucose as the sole carbon source. The wild type data are obtained from the same cultures as used by Boer et al. (2003) (2). The data represented are obtained from independent duplicate (TAM) or triplicate (wild type) chemostat cultivations. The gray bars correspond to the wild type, whereas the black bars correspond to the TAM strain (e.g., GCSI strain).
Figure 6:
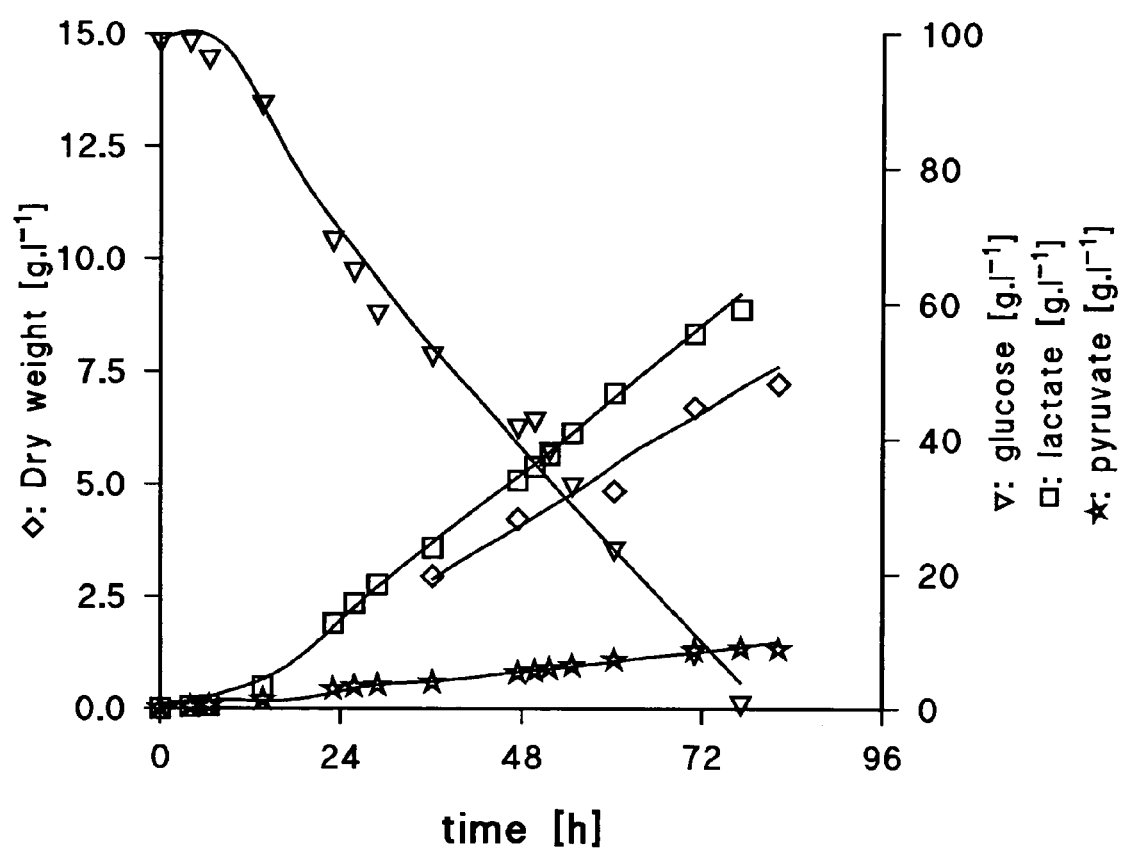
FIG. 6 The first phase of fermentation 1: dry weight, glucose, lactate and pyruvate concentrations as a function of the batch age. The aeration rate of the batch was fixed, using a mixture of 70 ml air/min and 430 ml $N_2$/min air. From 24 hours the oxygen feed or supply was limiting FIG. 7 The first and second phase of fermentation 1: dry weight, glucose, lactate and pyruvate concentrations as a function of the batch age. The aeration rate of the batch was fixed, using a mixture of 70 ml air/min and 430 ml $N_2$/min. From 24 hours the oxygen concentration was limiting upon depletion of the initial glucose, additional glucose was added, as powder, once again yielding a concentration of 100 g glucose.l$^{-1}$.
Figure 7:
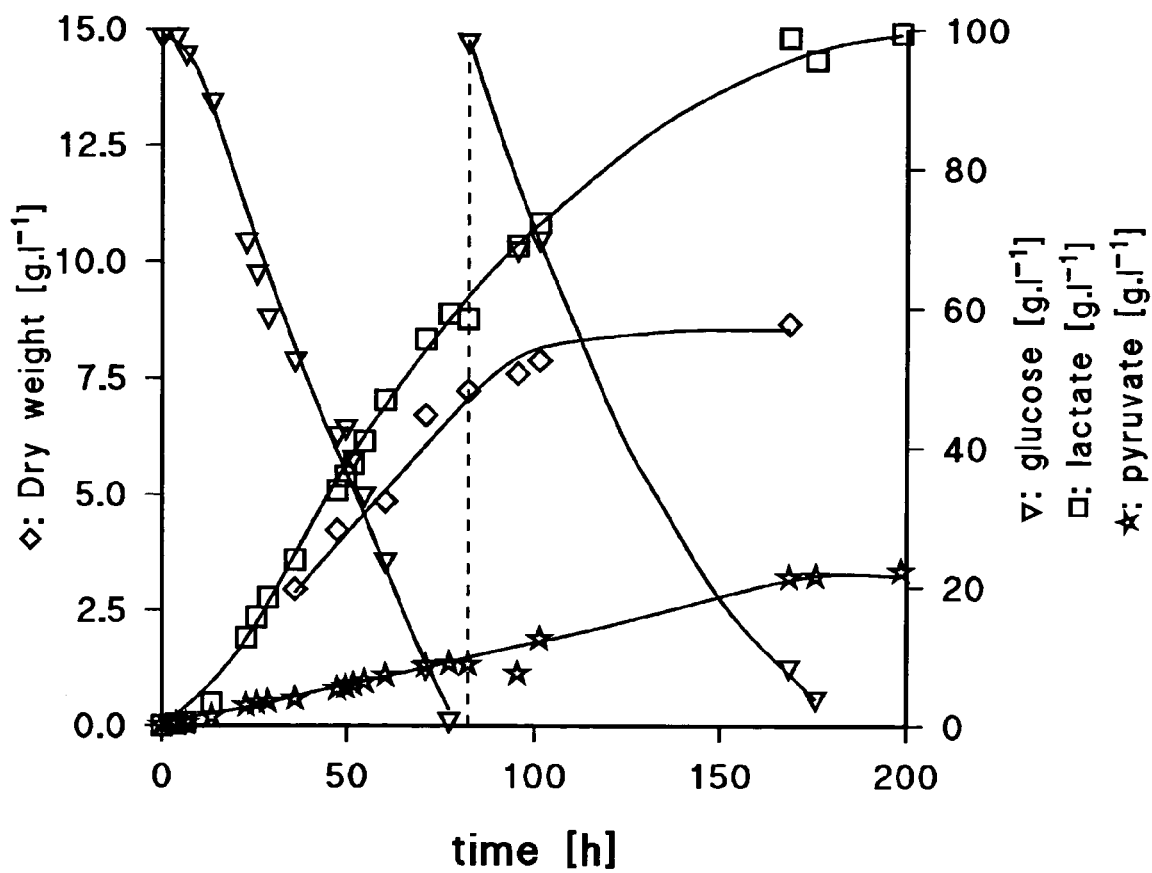
Figure 8:
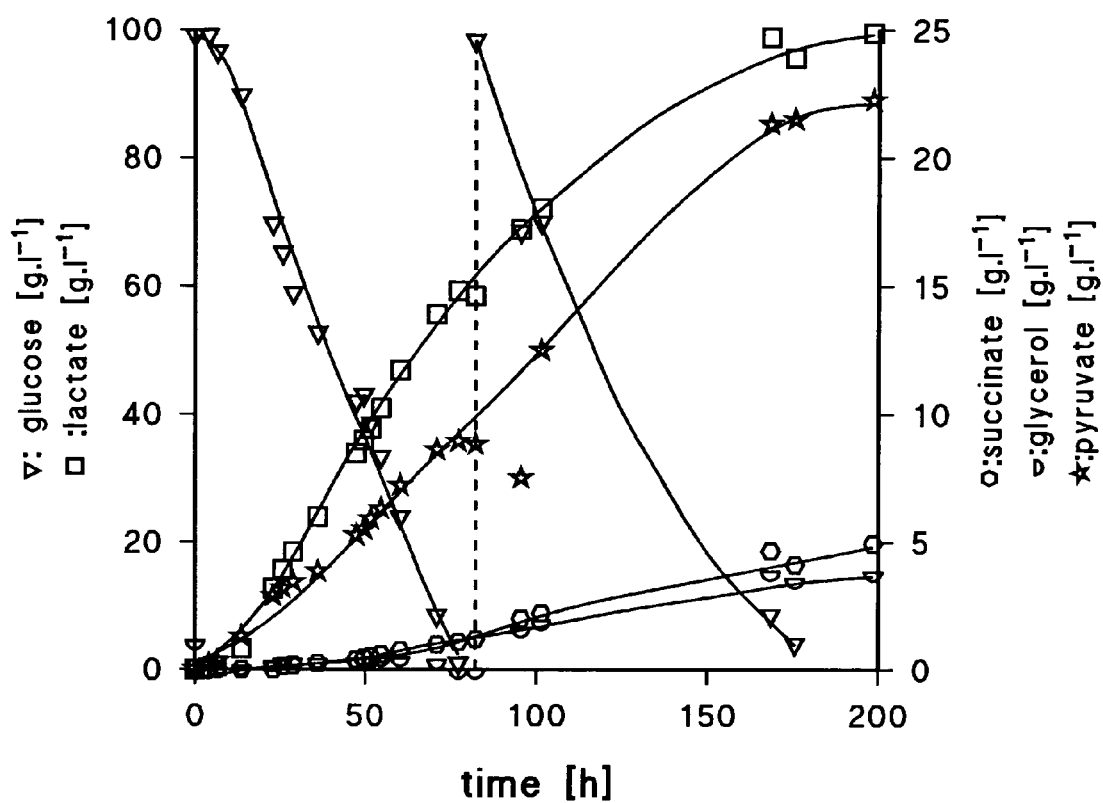
FIG. 8 The first and second phase of fermentation 1: glucose, lactate, pyruvate, succinate and glycerol concentrations as a function of the batch age. The aeration rate of the batch was fixed, using a mixture of 70 ml air/min and 430 ml $N_2$/min. From 24 hours the oxygen concentration was limiting upon depletion of the initial glucose, additional glucose was added, as powder, yielding a concentration of 100 gl$^{-1}$.
Figure 9:
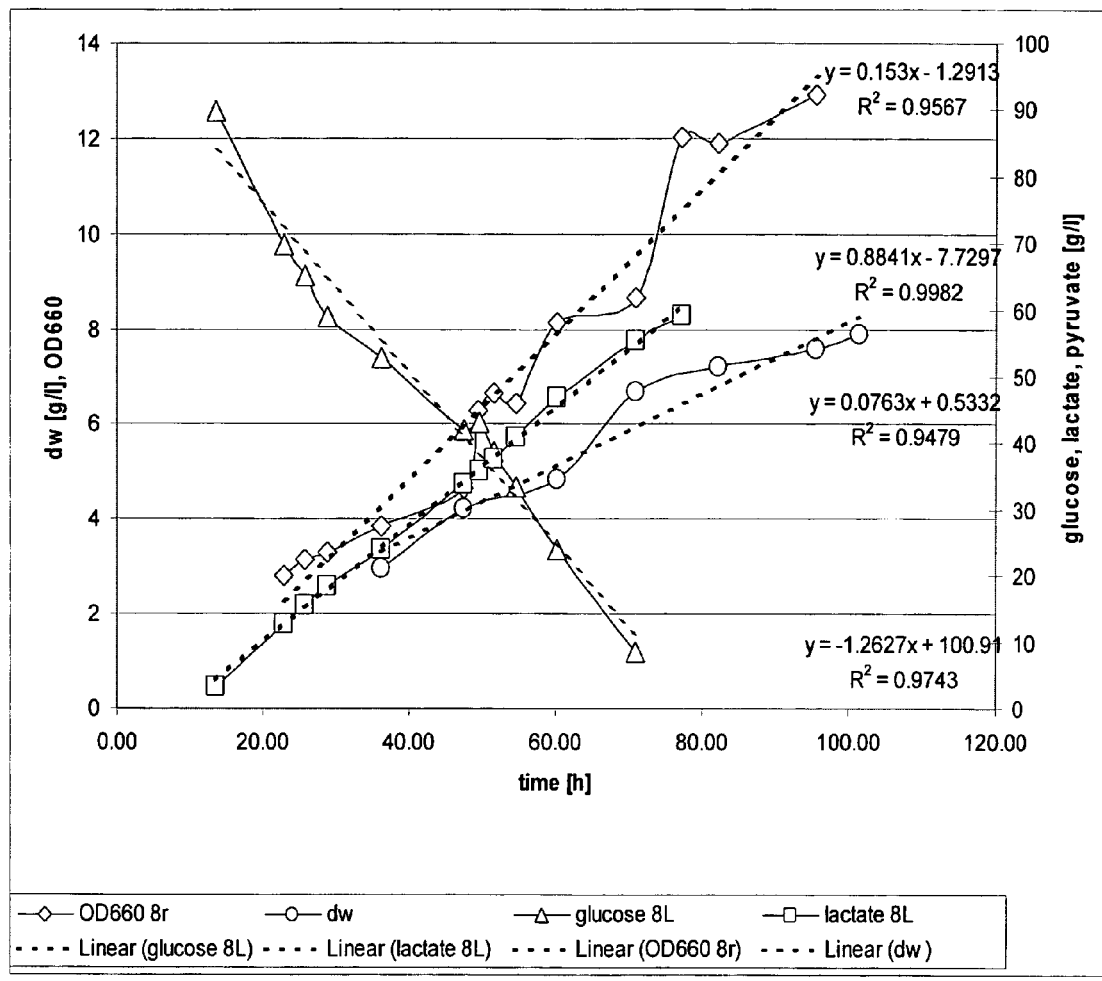
FIG. 9 Fermentation 1: dry weight, glucose, lactate and pyruvate concentrations between 24 and 82 hours (during which time the oxygenation becomes limiting as a function of the batch age).
Figure 10:
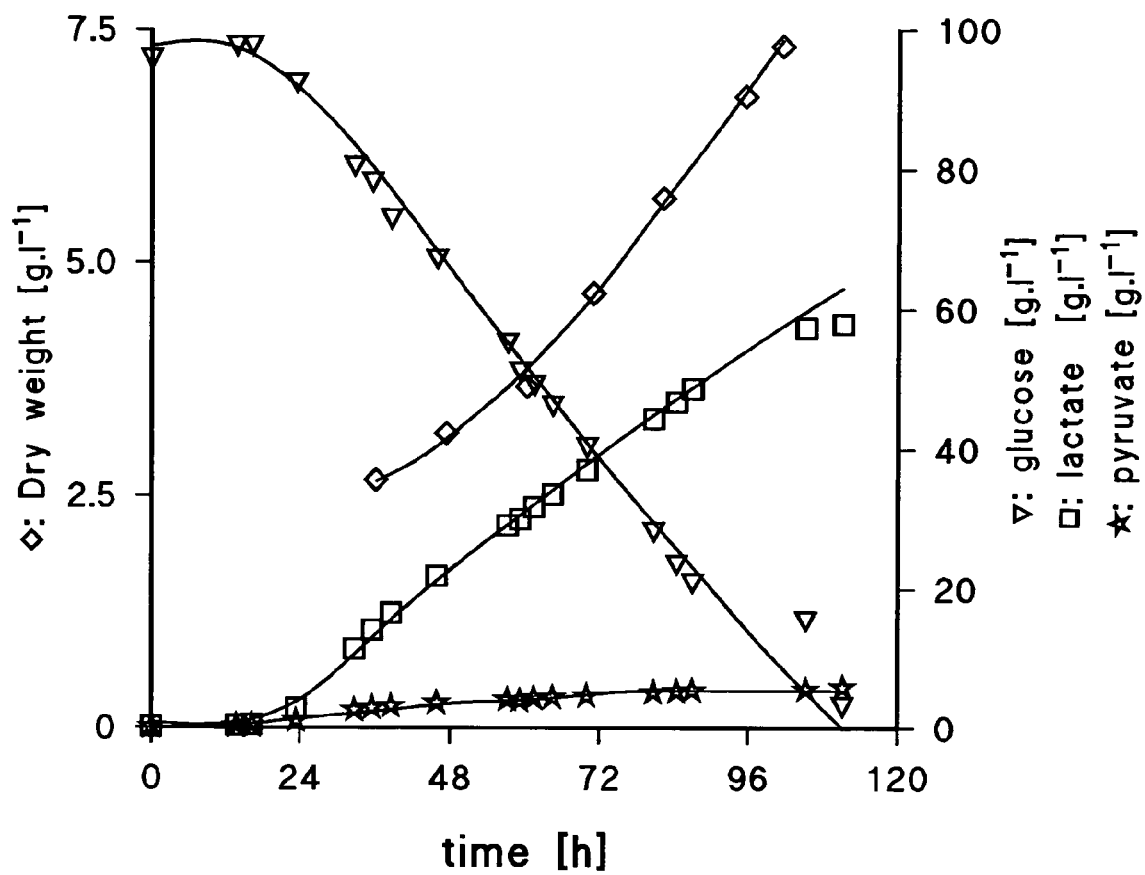
FIG. 10 The first phase of fermentation 2: dry weight, glucose, lactate and pyruvate concentrations as a function of the batch age. The aeration rate of the batch was fixed, using a mixture of 70 ml air/min and 430 ml $N_2$/min. From 24 hours the oxygen concentration was limiting FIG. 11 The first and second phase of fermentation 2: dry weight, glucose, lactate and pyruvate concentrations as a function of the batch age. The aeration rate of the batch was fixed, using a mixture of 70 ml air/min and 430 ml $N_2$/min. From 24 hours the oxygen concentration was limiting. Upon depletion of the initial glucose, additional glucose was added, as powder, yielding a concentration of 100 gl$^{-1}$.
Figure 11:
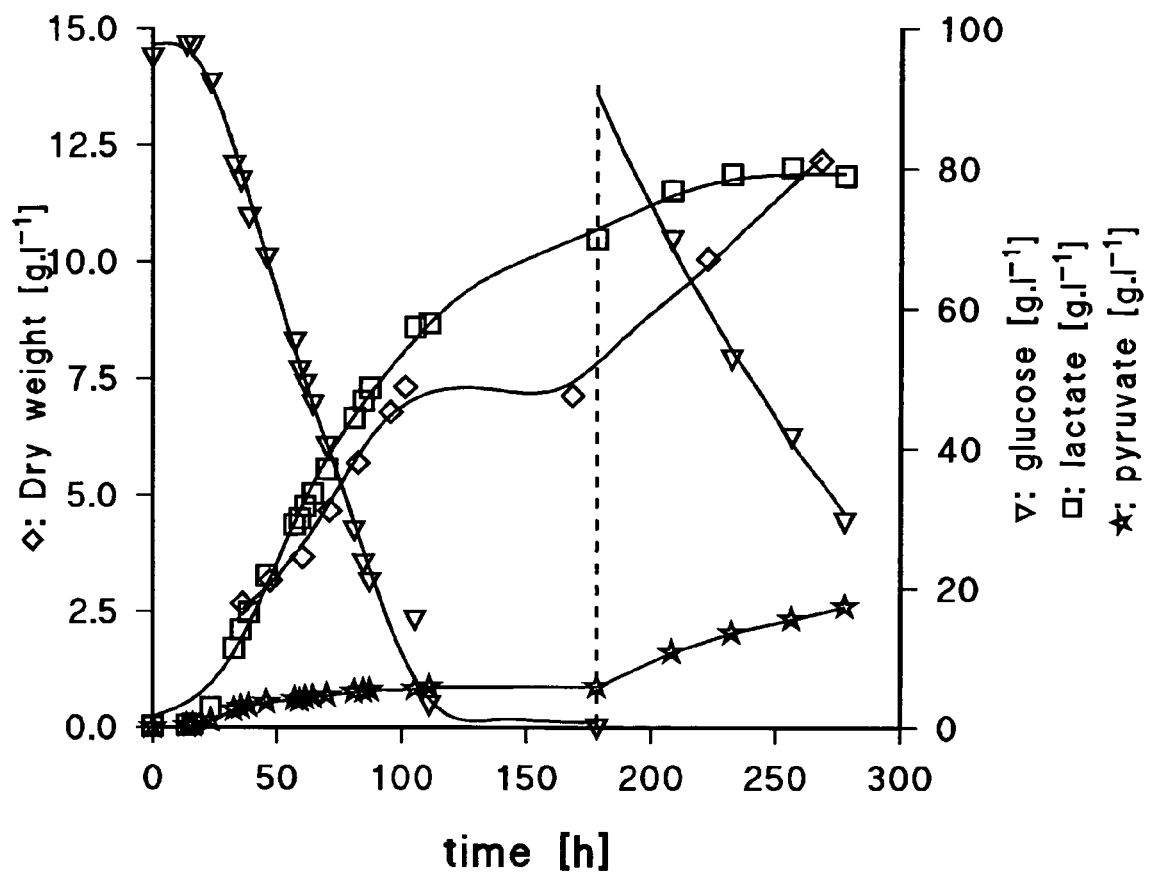
Figure 12:
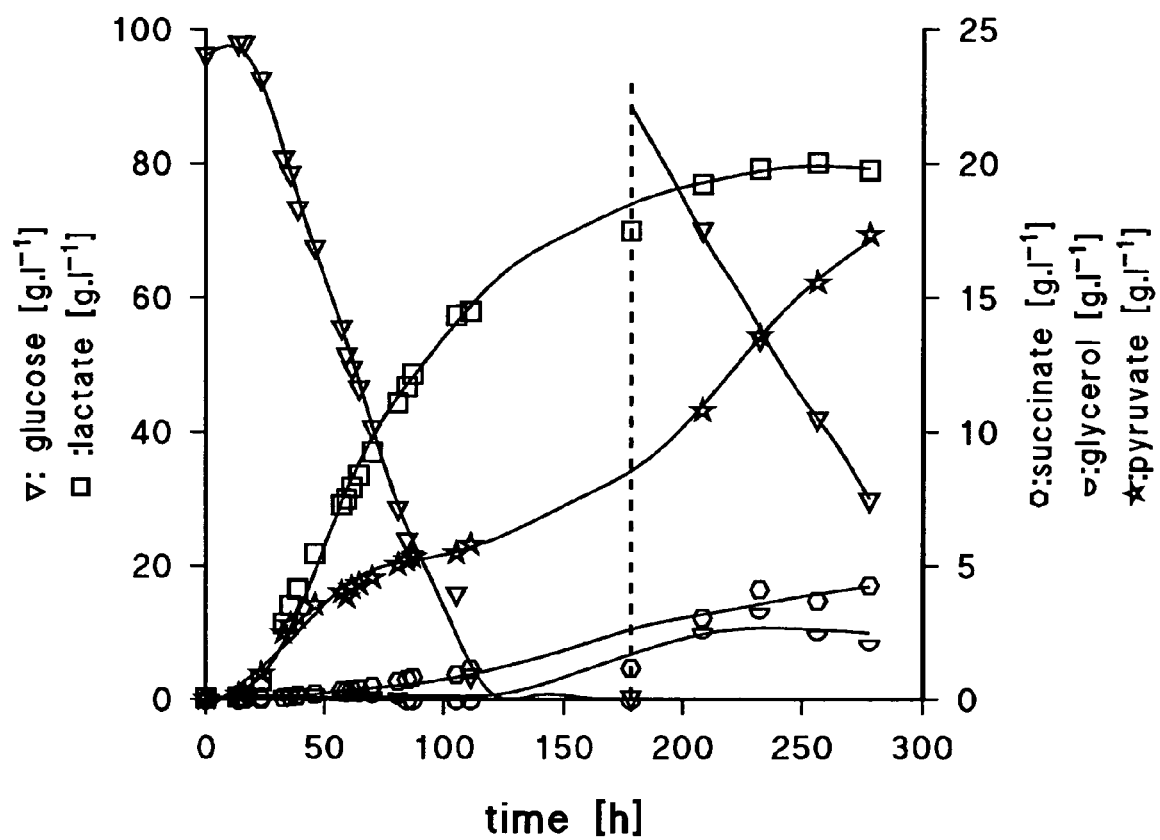
FIG. 12 The first and second phase of fermentation 2: glucose, lactate, pyruvate, succinate and glycerol concentrations as a function of the batch age. The aeration rate of the batch was fixed, using a mixture of 70 ml air/min and 430 ml $N_2$/min. From 24 hours the oxygen concentration was limiting. Upon depletion of the initial glucose, additional glucose was added, as powder, yielding a concentration of 100 gl$^1$.
Figure 13:
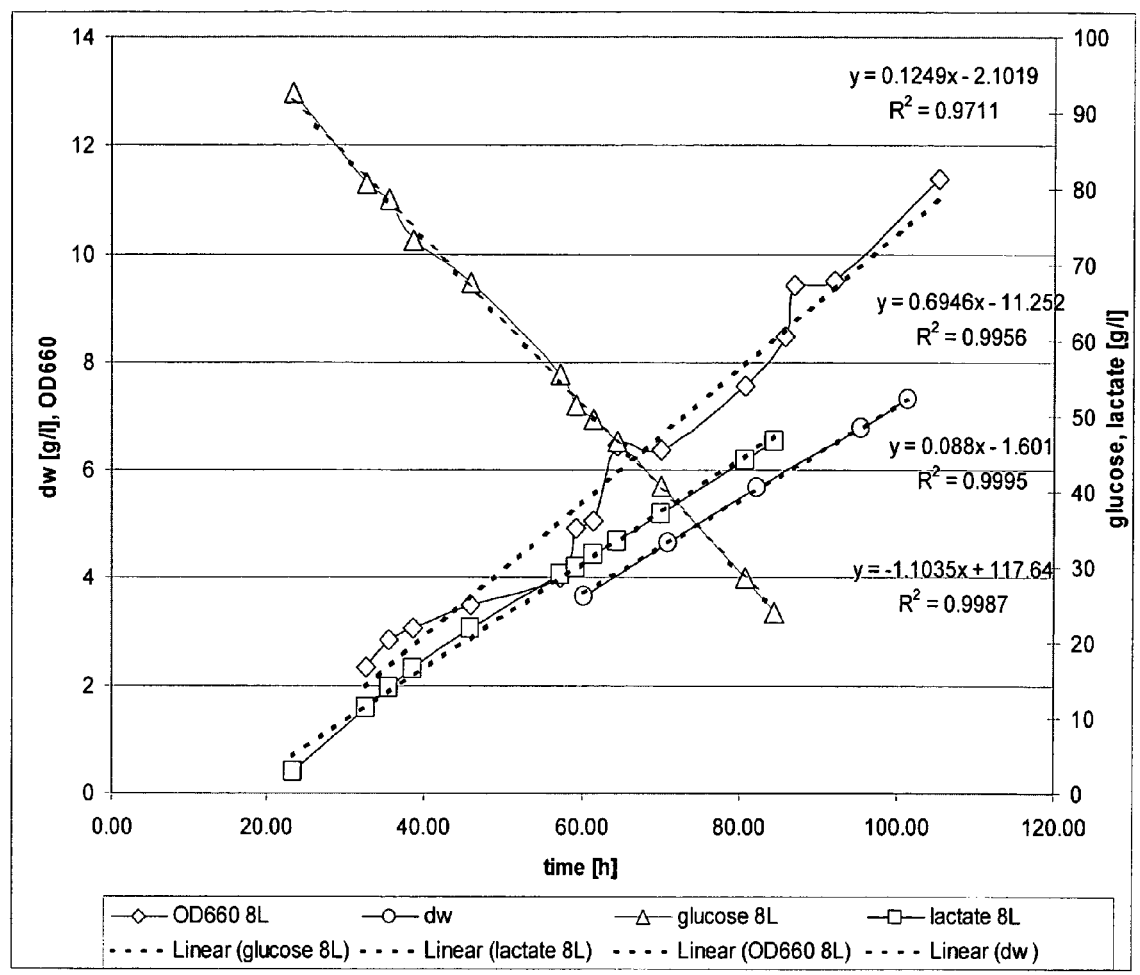
FIG. 13 Fermentation 2: dry weight, glucose, lactate and pyruvate concentrations between 24 and 82 hours, (during which time the oxygenation becomes limiting as a function of the batch age).

A striking observation was the change in expression of the genes coding for the hexose transporters. In spite of the high glucose concentrations under nitrogen limitation the low affinity transporters (HXT1 and HXT3) were down regulated 50-fold in the TAM strain compared to the wild type (FIG. 5). The known high affinity transporters (HXT6 and HXT7) were also downregulated (4 fold) in this strain (FIG. 5). As a result, the summed transcript abundance of all HXT's represented on the arrays (HXT1-10. HXT12, HXT14 and HXT16) is four times lower in the TAM strain under nitrogen limitation than in the wild type. In the glucose-responsive regulatory network of the HXT's (16), the only significant transcriptional change was the 12 fold downregulation of STD1, a glucose concentration-dependent modulator of expression, in the TAM strain compared to the wild type.

Since the TAM strain was not only glucose tolerant but also independent of $C_2$-compounds for growth on glucose, it is of interest to know to what extent transcriptional changes are responsible for the obtained $C_2$ carbon source-independence. The transcript abundance of GLY1, a previously demonstrated source of cytosolic $C_2$-compounds (24), was upregulated 2.5-fold in the TAM strain. However, the threonine aldolase activity in the TAM strain was still below the detection limit of 0.005 micromol/min mg protein$^{-1}$. In addition two genes (CAR1 and CAR2) of the arginine metabolism, which includes the reaction involving acetyl-CoA, were upregulated 6 fold in the TAM strain. To conclude the transcriptome analysis, it must be mentioned that a large group of upregulated genes in the selected Pdc negative strain were involved in mating (3 genes), meiosis (17 genes) and sporulation (8 genes). Since both the original strain (RWB837) and the selected Pdc negative strain are confirmed haploids, the mechanism behind and the origin of the expression of these genes, including the early meiotic transcription factor IME1, remains unknown. Sequence analysis of the upstream regions of the upregulated genes in the selected Pdc negative strain, also clearly showed an overrepresentation of the binding sites for UME6 and IME1, both involved in regulation of meiosis.

Metabolic fluxes in the TAM strain and wild type *Saccharomyces cerevisiae*.

During carbon-limited growth at a dilution rate of 0.1 h$^{-1}$ both the final TAM strain and wild type *Saccharomyces cerevisiae* displayed full respiratory glucose metabolism, although the biomass yield of the TAM strain was almost 10% lower. In nitrogen-limited chemostat cultures at a dilution rate of 0.1 h$^{-1}$, a more suitable environment to display the selected glucose-tolerant phenotype, the oxygen consumption rate of the TAM strain (4.0 mmol g biomass$^{-1}$ h$^{-1}$) was higher than that of the wild type (2.7 mmol g biomass$^{-1}$ h$^{-1}$) (Table 2). It is interesting to see, that the increase in the oxygen consumption (4.0−2.7=1.3 mmol g biomass$^{-1}$ h$^{-1}$) almost equals the oxygen required to regenerate the cytosolic NADH formed during pyruvate production (0.5×2.8=1.4 mmol g biomass$^{-1}$ h$^{-1}$). The rate of oxidative pyruvate metabolism by the mitochondria is apparently identical in the TAM strain and wild type *Saccharomyces cerevisiae* in nitrogen-limited chemostat cultures at this dilution rate.

An impression of the energetic efficiency of these nitrogen-limited cultures can be obtained by comparing the experimental biomass yield on ATP ($Y_{ATP}$) of the TAM strain (±8.3 g biomass mol ATP$^{-1}$) and the wild type (±6.8 g biomass mol ATP$^{-1}$). Although the Y ATP of the TAM strain is slightly higher than that of the wild type, the value for both nitrogen-limited cultures is around half the observed value under glucose-limited conditions (26), as was observed previously for other nitrogen-limited chemostat cultivations of *Saccharomyces cerevisiae* (11). The higher Y ATP combined with the oxidative regeneration of the NADH formed during pyruvate formation, results in a more than two-fold increase in the biomass yield on glucose of the TAM strain as compared to the wild type under nitrogen limitation.

It must be noted that there is an inconsistency in the fluxes of the nitrogen-limited chemostat cultivations of wild type *Saccharomyces cerevisiae* (Table 2). The carbon dioxide production rate was 13% higher than the summed ethanol-production- and oxygen-consumption rate (Table 2), whereas these values should be about equal. Judging from the relatively low recovery of consumed carbon, overestimation of the carbon dioxide formation is not a likely source of this deviation. Therefore, this discrepancy might be caused by underestimation of the evaporation of ethanol or other volatile compounds, e.g., acetaldehyde.

Hyperaccumulation of pyruvate by the selected TAM strain. The excretion of pyruvate by *Saccharomyces cerevisiae* with reduced or absent pyruvate decarboxylase activity has been observed before (6,17). The TAM strain, however, displays rapid growth on synthetic medium with glucose, whereas Pdc negative *Saccharomyces cerevisiae* strains do not grow under these conditions. In addition, the TAM strain also has the benefit of having no detectable amount of ethanol as a byproduct and it does, in contrast to many other pyruvate producing microorganisms, not require the addition or omission of specific compounds in the media (12). A culture of the TAM strain can produce a pyruvate concentration of at least about 135 g $l^{-1}$. The high specific rate of pyruvate production (6-7 mmol pyruvate g biomass$^{-1}$ h$^{-1}$) resulted in 100 g$l^{-1}$ of pyruvate, starting with a low density inoculum (OD660 of 0.1), after less than 60 h.

EXAMPLE 2

This example concerns the production characteristics of TAM strain transformed with YEpLpLDH. By using this strain as a host for the overexpression of a LDH gene the glycolytic flux can be at least partially redirected to lactate production.

The experiment involved two batch cultivations on mineral media with an oxygen limitation at 30° C. and pH 5.0 (titration with KOH 10 M).

Plasmid Construction

Amplification of the LDH Gene from *L. plantarum* Genomic DNA:

Genomic DNA was extracted from *L. plantarum* and a PCR was performed in order to amplify the LDH gene. The sequence for the LDH gene that was sequenced as part of the plasmid construct is listed as SEQ ID NO:3 below. The coding sequence amino acid sequence is listed as SEQ ID NO:4 below.

Oligos:

```
LDH fw
SEQ ID NO:1
5' TGA CTT ATT ATG TCA AGC AT 3'

LDH rev
SEQ ID NO:2
5' ATC GTA TGA AAT GAT TAT TTA TT 3'

PCR conditions:
95° C.       3'  ⎫
95° C.       1'  ⎬  x 33 cycles
48° C.       1'  ⎭
72° C.       2'
72° C.      10'
 4° C.       ∞
SEQ ID NO:3 (cds of gene 61-1023)
ggtaccacgc atgntgcaga cgcgttacgt atcggatcca gaattcgtga ttgacttatt     60 atg tca agc atg cca aat cat caa aaa gtt gtg tta gtc ggc gac ggc      108 gct gtt ggt tct agt tac gct ttt gcc atg gca caa caa gga att gct      156 gaa gaa ttt gta att gtc gat gtt gtt aaa gat cgg aca aag ggt gac      204 gcc ctt gat ctt gaa gac gcc caa gca ttc acc gct ccc aag aag att      252 tac tca ggc gaa tat tca gat tgt aag gac gct gac tta gtt gtt att      300 aca gcc ggt gcg cct caa aag cct ggt gaa tca cgt tta gac tta gtt      348 aac aag aat tta aat atc cta tca tcc att gtc aaa cca gtt gtt gac      396 tcc ggc ttt gac ggc atc ttc tta gtt gct gct aac cct gtt gac atc      444 tta act tac gct act tgg aaa ttc tca ggt ttc cca aag gat cgt gtc      492 att ggt tca ggg act tcc tta gac tct tca cgt tta cgc gtt gcg tta      540 ggc aaa caa ttc aat gtt gat cct cgt tcc gtt gat gct tac atc atg      588 ggt gaa cac ggt gat tct gaa ttt gct gct tac tca act gca acc atc      636 ggg aca cgt cca gtt cgc gat gtc gct aag gaa caa ggc gtt tct gac      684
```

-continued

```
gaa gat tta gcc aag tta gaa gat ggt gtt cgt aac aaa gct tac gac    732 atc atc aac ttg aag ggt gcc acg ttc tac ggt atc ggg act gct tta    780 atg cgg att tcc aaa gcc att tta cgt gat gaa aat gcc gtt tta cca    828 gta ggt gcc tac atg gac ggc caa tac ggc tta aac gac att tat atc    876 ggg act ccg gct gtg att ggt gga act ggt ttg aaa caa atc atc gaa    924 tca cca ctt tca gct gac gaa ctc aag aag atg caa gat tcc gcc gca    972 act ttg aaa aaa gtg ctt aac gac ggt tta gct gaa tta gaa aat aaa   1020 taa tcatttcata cgatatctga attcgtcgac aagcttctcg agcctaggct        1073
agctctagac cacacgtgtg ggggcccgag ctcgcggccg ctgt                  1117
```

SEQ ID NO:4
lactate dehydrogenase gene of L. Plantarum
Met Ser Ser Met Pro Asn His Gln Lys Val Val Leu Val Gly Asp Gly Ala Val Gly Ser Ser Tyr Ala Phe Ala Met Ala Gln Gln Gly Ile Ala Glu Glu Phe Val Ile Val Asp Val Val Lys Asp Arg Thr Lys Gly Asp Ala Leu Asp Leu Glu Asp Ala Gln Ala Phe Thr Ala Pro Lys Lys Ile Tyr Ser Gly Glu Tyr Ser Asp Cys Lys Asp Ala Asp Leu Val Val Ile Thr Ala Gly Ala Pro Gln Lys Pro Gly Glu Ser Arg Leu Asp Leu Val Asn Lys Asn Leu Asn Ile Leu Ser Ser Ile Val Lys Pro Val Val Asp Ser Gly Phe Asp Gly Ile Phe Leu Val Ala Ala Asn Pro Val Asp Ile Leu Thr Tyr Ala Thr Trp Lys Phe Ser Gly Phe Pro Lys Asp Arg Val Ile Gly Ser Gly Thr Ser Leu Asp Ser Ser Arg Leu Arg Val Ala Leu Gly Lys Gln Phe Asn Val Asp Pro Arg Ser Val Asp Ala Tyr Ile Met Gly Glu His Gly Asp Ser Glu Phe Ala Ala Tyr Ser Thr Ala Thr Ile Gly Thr Arg Pro Val Arg Asp Val Ala Lys Glu Gln Gly Val Ser Asp Glu Asp Leu Ala Lys Leu Glu Asp Gly Val Arg Asn Lys Ala Tyr Asp Ile Ile Asn Leu Lys Gly Ala Thr Phe Tyr Gly Ile Gly Thr Ala Leu Met Arg Ile Ser Lys Ala Ile Leu Arg Asp Glu Asn Ala Val Leu Pro Val Gly Ala Tyr Met Asp Gly Gln Tyr Gly Leu Asn Asp Ile Tyr Ile Gly Thr Pro Ala Val Ile Gly Gly Thr Gly Leu Lys Gln Ile Ile Glu Ser Pro Leu Ser Ala Asp Glu Leu Lys Lys Met Gln Asp Ser Ala Ala Thr Leu Lys Lys Val Leu Asn Asp Gly Leu Ala Glu Leu Glu Asn Lys Sub-Cloning of the Amplified PCR Fragment in an *E. coli* Vector (pSTblue-1, Producing pSTplLDH):

The unique fragment obtained was sub-cloned in the vector pSTblue-1 (commercially available and prepared bluntended opened in the EcoRV site), utilizing the kit: "Perfectly Blunt® Cloning Kit" (From Novagene). This subcloning step resulted in the plasmid: pSTplLDH Sequencing:

One of the plasmid obtained in this manner was sequenced, and the resulting nucleotide and aminoacid sequences were aligned with the deposited sequences (see the attached files).

Sub-Cloning of the Amplified Fragment into a *S. cerevisiae* Integrative Expression Vector (pYX022, Producing p022TLP):

From the obtained and sequenced plasmid pSTplLDH, the coding sequence of plLDH was excised by using the EcoRI restriction enzyme. Said obtained fragment was subsequently sub-cloned into the *S. cerevisiae* integrative expression vector pYX022 (R&D Systems), EcoRI opened and de-phosphorylated. The resulting expression plasmid was named: pYX022TLP. pYX022TLP was prepared by Paola Branduardi.

Plasmid pYX022TLP was cut with AatII and a linker was ligated into this site, replacing the AatII site with five new sites, XhoI, BamHI, SmaI/XmaI and NheI. The new plasmid, pYX022LpLDH-Aat, was digested with NheI and SacI. The fragment, containing the TPI1 promoter and the *L plantarum* LDH was ligated into YEplac195 cut with XbaI and SacI, resulting in YEpLpLDH (prepared by Ron Winkler).

Strains and Maintenance

The strain used was TAM with the yeast plasmid pLpLDH. The TAM host strain is as described above. YEpLpLDH comprises an LDH gene from a *Lactobacillus plantarum* strain functionally linked to a tpi promoter. TAM with the yeast plasmid pLpLDH was deposited in the permanent collection of the Northern Regional Research Center (NRRL), Agricultural Research Service Culture Collection, National Center for Agricultural Utilization Research, US Department of Agriculture, 1815 North University Street, Peoria, Ill. 61604, U.S.A. on Apr. 23, 2004 under the terms of the Budapest Treaty, and accorded the accession number NRRL Y-30742.

The strains were grown at 30° C. in shake flasks on a mineral medium with glucose. After 24 h, the culture was brought to 20% (v/v) glycerol with glycerol P.A. and stored in 2 ml vials at −80° C. These vials were used as inoculate for all subsequent experiments.

Media

TABLE 3

ME trace element solution
The concentrated trace element solution consisted of:

| Chemicals | Formula | $gl^{-1}$ | ml |
|---|---|---|---|
| EDTA (Titriplex III ®) | $C_{10}H_{14}N_2Na_2O_8 \cdot 2H_2O$ | 15.00 | |
| Zinc sulfate heptahydrate | $ZnSO_4 \cdot 7H_2O$ | 4.50 | |
| Manganese chloride dihydrate | $MnCl_2 \cdot 2H_2O$ | 0.84 | |
| Cobalt(II)chloride hexahydrate (Toxic) | $CoCl_2 \cdot 6H_2O$ | 0.30 | |
| Copper (II)sulphate pentahydrate | $CuSO_4 \cdot 5H_2O$ | 0.30 | |
| Di-sodium molybdenum dihydrate | $Na_2MoO_4 \cdot 2H_2O$ | 0.40 | |
| Calcium chloride dihydrate | $CaCl_2 \cdot 2H_2O$ | 4.50 | |
| Iron sulphate heptahydrate | $FeSO_4 \cdot 7H_2O$ | 3.00 | |
| Boric acid | $H_3BO_3$ | 1.00 | |
| Potassium iodide | KI | 0.10 | |
| Demineralized water | | | 1000 |

EDTA and $ZnSO_4 \cdot 7H_2O$ were dissolved in 750 ml of demineralized water and the pH was maintained at 6.0 with NaOH (p.a.). The other components were subsequently dissolved one by one, while maintaining the pH. Once dissolved the pH was adjusted to 4.0 with 1 M HCl and the volume was adjusted to 1 liter. The solution was sterilized at 121° C. for 20 minutes.

TABLE 4

ME vitamin solution
The concentrated vitamin solution consisted of:

| Chemicals | Formula | $gl^{-1}$ | ml |
|---|---|---|---|
| Biotin (D−) | $C_{10}H_{16}N_2O_3S$ | 0.05 | |
| Ca D(+) pantothenate | $C_{18}H_{32}CaN_2O_{10}$ | 1.00 | |
| Nicotinic acid | $C_6H_5NO_2$ | 1.00 | |
| Myo-inositol (for microbiology) | $C_6H_{12}O_6$ | 25.00 | |
| Thiamine chloride hydrochloride | $C_{12}H_{18}Cl_2N_4OS \cdot xH_2O$ | 1.00 | |
| Pyridoxol hydrochloride | $C_8H_{12}ClNO_3$ | 1.00 | |
| p-aminobenzoic acid | $C_7H_7NO_2$ | 0.20 | |
| Demineralized water | | | 1000 |

The biotin was dissolved in 10 ml of 0.1 M NaOH solution. 750 ml of demineralized water was added to this solution and the pH was adjusted to 6.5 with 1 M HCl. All of components in the latter solution were dissolved, one by one, whilst continuously to maintain the pH at 6.5. After all components were added the volume was adjusted to 1000 ml, pH 6.5.

TABLE 5

Batch mineral medium with glucose
The batch medium in the fermenter consisted of:

| Chemicals | Formula | Gram | Liter |
|---|---|---|---|
| Ammonium sulphate | $(NH_4)_2SO_4$ | 10.0 | |
| Potassium dihydrogen phosphate | $KH_2PO_4$ | 6.0 | |
| Magnesium sulfate $\cdot 7H_2O$ | $MgSO_4 \cdot 7H_2O$ | 1.0 | |
| ME-trace | | | 0.002 |
| Silicone antifoam | | | 0.0002 |
| Demineralized water added after sterilization | | | 1.0 |
| ME-vitamins | | | 0.002 |
| glucose $\cdot H_2O$ | $C_6H_{12}O_6 \cdot H_2O$ | 110 | |
| Demineralized water | | | 0.200 |

Shake Flask Cultivations

The shake flask experiments were conducted in round bottom flasks at a temperature of 30° C. in a rotary shaker. Aerobic conditions were maintained by shaking at 200 rpm and filling the shake flasks 500 ml total volume to ⅕ of their capacity.

Fermenter Cultivations

The fermenter cultivations were carried out in bioreactors with a working volume of 1 liter (Applikon Dependable Instruments, Schiedam, The Netherlands). The pH was automatically controlled at pH 5.0 by titration with 10 M potassium hydroxide. The added amount of potassium hydroxide was determined on the basis of weight (Balance Mettler Toledo PB3001-5, Tiel). The temperature was maintained at 30° C. by circulating heated water through a heating finger. Anti-foam was added to the medium, Silicone (BDH, Poole England).

The stirrer speed, using two Rushton impellers, was kept constant at 800 rpm. The gas flow was maintained at 0.5 $l.min^{-1}$, and consisted of 70 ml air/min and 430 ml $N_2$ gas/min using two Brooks 5876 mass-flow controllers (Brooks BV, Veenendaal, The Netherlands).

The pH, DOT (dissolved oxygen tension) and KOH feeds were monitored continuously using an on-line data acquisition & control system (Bioscada, Developed in-house at the TUDelft).

Batch Conditions

During the batch fermentation two different stages were distinguished. As the oxygenation was kept constant the strain grew at maximum growth rate until the oxygen became limiting Upon oxygen limitation, biomass formation, lactate production and glucose consumption became linear until the glucose was depleted.

Upon depletion of the glucose additional glucose was added as a powder to 100 g $l^{-1}$.

The pH, DOT and KOH feeds were monitored continuously using an on-line data acquisition & control system (Bioscada, Developed in-house at the TUDelft).

Off-Gas Analysis

The exhaust gas of the fermenter cultivations was cooled in a condenser (2° C.) and dried with a Perma Pure dryer (type PD-625-12P). Oxygen and carbon dioxide concentrations were determined with an ADC 7000 gas analyser. The exhaust gas flow rate was measured with a Saga Digital Flow meter (Ion Science, Cambridge) Specific rates of carbon dioxide production and oxygen consumption were calculated as previously described (28).

Sample Preparation

Samples for biomass, substrate and product analysis were collected on ice. Samples of the fermentation broth and cell free samples (prepared by centrifugation at 10.000×g for 10 minutes) were stored at −20° C. for later analysis.

HPLC Determinations

Presence of sugars, organic acids and polyols were determined simultaneously using a Waters HPLC 2690 system equipped with an HPX-87H Aminex ion exclusion column (300×7.8 mm, BioRad) (60° C., 0.6 ml/min 5 mM H2SO4). Coupled to a Waters 2487 UV detector and a Waters 2410 refractive index detector.

Determination of Dry Weight

The dry weight of yeast in the cultures was determined by filtering through 5 ml of culture on a 0.45 µm filter (Gelman sciences). The sample was, when necessary, diluted to an end-concentration of between 5 and 10 g 1-1. The filters were kept in an 80° C. incubator for at least 24 hours, so that their dry weight could be measured before use. The yeast cells in the sample were retained on the filter and washed with 10 ml of demineralized water. The filter with the cells was then dried in a microwave oven (Amana Raderrange, 1500 Watt) for 20 minutes at 50% capacity. The dried filter with the cells was weighed after cooling for 2 minutes. The dry weight was calculated by subtracting the weight for the filter from the weight of the filter with cells.

Determination of Optical Density ($OD_{660}$)

The optical density of the yeast cultures was determined at 660 nm with a spectrophotometer; Novaspec II (Amersham Pharmacia Biotech, Buckinghamshire, UK) in 4 ml cuvettes. When necessary the samples were diluted to yield an optical density of between 0.1 and 0.3.

A summary of the results of the fermentation experiments is shown in tables 6a and 6b. A detailed description of the individual fermentations is shown in the tables and FIGS. 6-13.

The oxygen limitation that was achieved, after 24 hours, by fixing the amount of oxygenation for both fermentations resulted in a linear consumption profile for glucose as well as a linear production profile for lactate.

Fermentation 1

The batch starting with an initial concentration of 99.2 g glucose.$l^{-1}$ was inoculated from a shake flask preculture. During the first 24 hours of the batch fermentation oxygenation was not limiting as the biomass increased exponentially at 0.13±0.02 $h^{-1}$. Following this phase oxygen became limiting as the glucose consumption and the production of biomass, lactate, pyruvate and succinate exhibited a linear trend (see table 1 and FIG. 1 to 5). The consumption of the initial glucose concentration took 80 hours. The lactate. productivity during this phase was 0.69 g.l.$h^{-1}$ with a specific productivity of 0.53 g $g^{-1}$ $h^{-1}$ and a yield on glucose of 0.63 g $g^{-1}$. The pyruvate productivity was 0.05 g $l^{-1}$ $h^{-1}$ with a specific productivity of 0.07 g $g^{-1}$ $h^{-1}$ and a yield on glucose of 0.045 g $g^{-1}$. See FIGS. 6-9.

After exhaustion of the first batch of glucose additional glucose is added as powder resulting in a glucose concentration 98.4 g glucose $l^{-1}$. The lactate productivity during this phase was 0.039 g $l^{-1}h^{-1}$ with a specific productivity of 0.56 g $l^{-1}$ $h^{-1}$ and a yield on glucose of 0.42 g $g^{-1}$. The pyruvate productivity was 0.15 g $l^{-1}$ $h^{-1}$ with a specific productivity of 0.26 g $g^{-1}h^{-1}$ and a yield on glucose of 0.15 g $g^{-1}$. The overall productivity of lactate was 100 g $l^{-1}h^{-1}$ was obtained with an overall yield of 0.48 g $g^{-1}$ and a specific lactate productivity of 0.53 g $g^{-1}h^{-1}$.

Fermentation 2

The batch starting with an initial concentration of 96.3 g glucose $l^{-1}$ was inoculated from a shake flask preculture. During the first 24 hours of the batch fermentation oxygenation was not limiting as the biomass increased exponentially TABLE 6a Overview of the results of batch 1

| exp. | time [h] | production biomass [g·$l^{-1}$·$h^{-1}$] | production biomass [OD660·$l^{-1}$·$h^{-1}$] | production lactate [g·$l^{-1}$·$h^{-1}$] | production pyruvate [g·$l^{-1}$·$h^{-1}$] | production glycerol [g·$l^{-1}$·$h^{-1}$] | production succinate [g·$l^{-1}$·$h^{-1}$] | specific productivity lactate [g·$g^{-1}$·$h^{-1}$] | specific productivity pyruvate [g·$g^{-1}$·$h^{-1}$] | Yield dry weight on gluc. $Y_{XB}$ [g·$g^{-1}$] | Yield lactate on gluc. $Y_{XB}$ [g·$g^{-1}$] | Yield pyruvate on gluc. $Y_{XB}$ [g·$g^{-1}$] |
|---|---|---|---|---|---|---|---|---|---|---|---|---|
| 1 | 24-80 #1 | 0.09 | 0.12 | 0.69 | 0.050 | 0 #2 | 0.012 | 0.53 | 0.070 | 0.079 | 0.63 | 0.045 |
| 1 | 80-175 #3 | 0.015 | 0.04 | 0.39 | 0.15 | 0.03 | 0.033 | 0.56 | 0.26 | 0.016 | 0.42 | 0.15 |

1: Between 24-80 hour oxygen transfer is assumed limiting
2: Glycerol concentration is constant
3: Second phase after addition of additional glucose TABLE 6b Overview of the results of batch 2

| exp. | time | production biomass [g·$l^{-1}$·$h^{-1}$] | production biomass [OD660·$l^{-1}$·$h^{-1}$] | production lactate [g·$l^{-1}$·$h^{-1}$] | production pyruvate [g·$l^{-1}$·$h^{-1}$] | production glycerol [g·$l^{-1}$·$h^{-1}$] | production succinate [g·$l^{-1}$·$h^{-1}$] | specific productivity lactate [g·$g^{-1}$·$h^{-1}$] | specific productivity pyruvate [g·$g^{-1}$·$h^{-1}$] | Yield dry weight on gluc. $Y_{XB}$ [g·$g^{-1}$] | Yield lactate on gluc. $Y_{XB}$ [g·$g^{-1}$] | Yield pyruvate on gluc. $Y_{XB}$ [g·$g^{-1}$] |
|---|---|---|---|---|---|---|---|---|---|---|---|---|
| 2 | 24-80 | 0.08 | 0.15 | 0.88 | 0.120 | 0.019 | 0.019 | 0.22 | 0.020 | 0.060 | 0.70 | 0.093 |

1: Between 24-80 hour oxygen transfer is assumed limiting at $0.13\pm0.02$ $h^{-1}$. Following this phase oxygen became limiting as the glucose consumption and the production of biomass, lactate, pyruvate and succinate exhibited a linear trend (see table 1 and FIG. 1 to 5). The consumption of the initial glucose concentration took 106 hours. This was over 30 hours longer than the duplicate fermentation indicating a more severe oxygen limitation. The lactate productivity during this phase was 0.88 g $l^{-1}$ $h^{-1}$ with a specific productivity of 0.22 g $g^{-1}h^{-1}$ and a yield on glucose of 0.70 g $g^{-1}$. The pyruvate productivity was 0.12 g $h^{-1}$ with a specific productivity of 0.22 g $g^{-1}h^{-1}$ and a yield on glucose of 0.093 g $g^{-1}$. See FIGS. 10-13.

EXAMPLE 3

This example concerns the production characteristics of TAM strain transformed with YEpLpLDH. The experiment involved batch cultivations on mineral media at 32° C. and without pH control.

Strains

The strain used was TAM with the yeast plasmid pLpLDH. The TAM host strain is as described above. YEpLpLDH comprises an LDH gene from a *Lactobacillus plantarum* strain functionally linked to a tpi promoter, and is described above.

The strains were grown at 32° C. in shake flasks on a mineral medium with glucose. The fermentation was carried out in 250 ml triple baffled shake flasks containing 100 ml medium. The medium composition is tabulated below.

Media

Glucose 75 g/L, trace elements, vitamins and salts listed below.

TABLE 7

The trace elements consisted of:

| Formula | $\mu gl^{-1}$ |
|---|---|
| $ZnSO_4 \cdot 7H_2O$ | 712 |
| $CuSO_4 \cdot 5H_2O$ | 62.5 |
| $Na_2MoO_4 \cdot 2H_2O$ | 235 |
| $H_3BO_3$ | 500 |
| $MnSO_4 \cdot H_2O$ | 450 |
| $FeCl_3$ | 200 |
| KI | 100 |

TABLE 8

The vitamins consisted of:

| Chemicals | $\mu gl^{-1}$ |
|---|---|
| Biotin (D-) | 2 |
| Ca D(+) pantothenate | 400 |
| Inositol | 2000 |
| Folic acid | 2 |
| Thiamine hydrochloride | 400 |
| Pyridoxine hydrochloride | 400 |
| p-aminobenzoic acid | 200 |
| Riboflavin | 200 |
| Niacin | 400 |

TABLE 9

The salts:

| Chemicals | $gl^{-1}$ |
|---|---|
| Urea | 1 |
| $KH_2PO_4$ | 1 |
| $MgSO_4 \cdot 7H_2O$ | 0.5 |
| NaCl | 0.1 |
| $CaCO_3$ | 2.78 |
| $CaCl_2$ | 0.1 |

Figure 14:
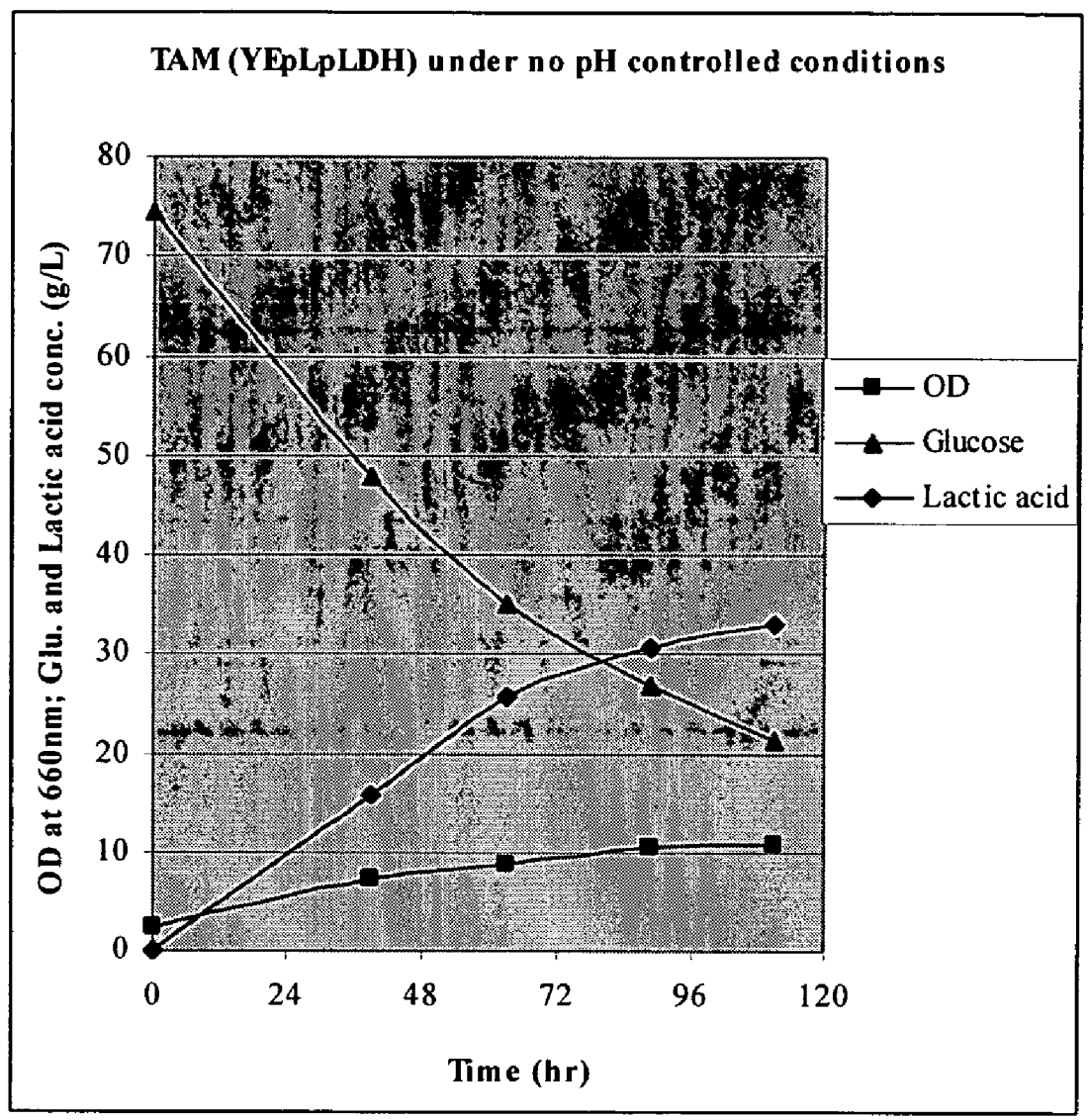
FIG. 14A graph of lactate and glucose concentration over 111 hours when a TAM YEpLpLDH is cultured in batch culture without the pH being controlled.

Glucose was made in 50% stock solution and autoclaved separately. A certain amount of $Ca^{+2}$ was added to better maintain the cells in active physiological stage. In this example, a total of 1112 ppm $Ca^{+2}$ had been added. Fermentation was carried out at 32C with 180 rpm shaking in a New Brunswick G-25 shaker. The results for TAM YEpLpLDH are depicted in Table 10 below and in FIG. 14.

TABLE 10

| Time (hr) | $OD_{660}$ | pH | Glucose g/L | Lactate g/L |
|---|---|---|---|---|
| 0 | 2.47 | 5.86 | 74.47 | 0 |
| 39 | 7.38 | 3.01 | 47.80 | 15.9 |
| 63 | 8.70 | 2.80 | 35.08 | 25.74 |
| 88.5 | 10.48 | 2.72 | 26.80 | 30.78 |
| 111 | 10.72 | 2.67 | 21.28 | 32.88 |

As can be seen in the table and the graph, the rate of lactic acid formation decreased after 63 hours. Longer fermentation times (from 63 up to 111 hours) only increased the concentration of lactate by another 7.14 g/L. The yield (wt/wt) on a glucose basis was 62.8%.

REFERENCES

The following references, to the extent that they provide exemplary procedural or other details supplementary to those set forth herein, are specifically incorporated herein by reference.

1. Barnett Payne and Yarrow. 1995. *Yeasts: characterization and identification*, $2^{nd}$ edition, Cambridge University Press ISBN 052135056.
2. Boer, V. M., Jh. de Winde, J. T. Pronk, M. D. W. Piper. 2002. The genome-wide transcriptional responses of *Saccharomyces cerevisiae* grown on glucose in aerobic chemostat cultures limited for carbon, nitrogen, phosphorous or sulfur. J. Biol. Chem 278(5):3265-3274.
3. Dykhuizen, D. E. and D. L. Hartl. 1983. Selection in chemostat cultures. Microbiol.Rev.47: 150-168.
4. Flikweert, M. T., M. de Swaaf, J. P. van Dijken, and J. T. Pronk. 1999. Growth requirements of pyruvate-decarboxylase-negative *Saccharomyces cerevisiae*. FEMS Microbiol. Lett. 174:73-79.
5. Flikweert, M. T., L. van der Zanden, W. M. T. M. Janssen, H. Y. Steensma, J. P. van DUken, and J. T. Pronk. 1996. Pyruvate decarboxylase: an indispensable enzyme for growth of *Saccharomyces cerevisiae* on glucose. Yeast 12:247-257.
6. Flikweert, M. T., J. P. van Dijken, and J. T. Pronk. 1997. Metabolic response of pyruvate-decarboxylase-negative *Saccharomyces cerevisiae* to glucose excess. Appl. Environ. Microbiol. 63:3399-3404.
7. Gancedo, J. M. 1998. Yeast carbon catabolite repression. Microbiol.Mol.Biol.Rev.62:334-361.

8. Gietz, R. D. and A. Sugino. 1988. New yeast-*Escherichia coli* shuttle vectors constructed with in vitro mutagenized yeast genes lacking six-base pair restriction sites. Gene 74:527-534.
9. Gietz, R. D. and R. A. Woods. 2002. Transformation of yeast by lithium acetate/single-stranded carrier DNA/polyethylene glycol method. Methods in enzymology 350:87-96.
10. Harder, W., J. G Kuenen, and A. Matin. 1977. Microbial selection in continuous culture. J. Appl. Bacteriol. 43: 1-24.
11. Larsson, C., U. von Stockar, I. Marison, and L. Gustafsson. 1993. Growth and metabolism of *Saccharomyces cerevisiae* in chemostat cultures under carbon-, nitrogen-, or carbon- and nitrogen-limiting conditions. J. Bacteriol. 175: 4809-4816.
12. Li, Y., J. Chen, and S. Y. Lun. 2001. Biotechnological production of pyruvic acid. Appl. Microbiol. Biotechnol. 57:451-459.
13. Miyata, R. and T. Yonehara. 1999. Breeding of high-pyruvate-producing *Torulopsis* glabrata with acquired reduced pyruvate decarboxylase. J. Biosci. Bioeng 88: 173-178.
14. *Piper*, M. D. W., P. Daran-Lapujade, C. Bro, B. Regenberg, S. Knudsen, J. Nielsen, and J. T. Prank. 2002. Reproducibility of oligonucleotide microarray transcriptome analyses: an interlaboratory comparison using chemostat cultures of *Saccharomyces cerevisiae*. J.Biol.Chem.277: 37001-37008.
15. Pronk, J. T. 2002. Auxotrophic yeast strains in fundamental and applied research. Appl. Environ. Microbiol. 68:2095-2100.
16. Rolland, F., J. Winderickx, and J. M. Thevelein. 2002. Glucose-sensing and -signaling mechanisms in yeast. FEMS Yeast Res. 2:183-201.
17. Schmitt, H. D. and F. K. Zimmermann. 1982. Genetic analysis of the pyruvate decarboxylase reaction in yeast glycolysis. J.Bacteriol.151:1146-1152.
18. Tusher, V. G, R. Tibshirani, and G Chu. 2001. Significance analysis of microarrays applied to the ionizing radiation response. Proc. Natl. Acad. Sci. USA 98:5116-5121.
19. van Dijken, J. P., J. Bauer, L. Brambilla, P. Duboc, J. M. Francois, C. Gancedo, M. L. F. Giuseppin, J. J. Heijnen, M. Hoare, H. C. Lange, E. A. Madden, P. Niederberger, J. Nielsen, J. L. Parrou, T. Petit, D. Porro, M. Reuss, N. van Riel, M. Rizzi, H. Y. Steensma, C. T. Verrips, J. Vindelov, and J. T. Pronk. 2000. An interlaboratory comparison of physiological and genetic properties of four *Saccharomyces cerevisiae* strains. Enzyme Microb. Technol. 26:706-714.
20. van Helden, J., B. Andre, and J. Collado-Vides. 2000. A web site for the computational analysis of yeast regulatory sequences. Yeast 16:177-187.
21. van Hoek, P., M. T. Flikweert, Q. J. M. van der Aart, H. Y. Steensma, J. P. van Dijken, and J. T. Pronk. 1998. Effects of pyruvate decarboxylase overproduction on flux distribution at the pyruvate branchpoint in *Saccharomyces cerevisiae*. Appl. Environ. Microbiol. 64:2133-2140.
22. van Hoek, P., J. P. van Dijken, and J. T. Pronk. 2000. Regulation of fermentative capacity and levels of glycolytic enzymes in chemostat cultures of *Saccharomyces cerevisiae*. Enzyme Microb. Technol. 26:724-736.
23. van Maris, A. J. A., B. M. Bakker, M. Brandt, A. Boorsma, M. J. Teixeira de Mattos, A. R. Grivell, J. T. Pronk, and J. Blom. 2001. Modulating the distribution of fluxes among respiration and fermentation by overexpression of HAP4 in *Saccharomyces cerevisiae*. FEMS Yeast Research 1:139-149.
24. van Maris, A. J. A, M. Ah. Luttik, A. A. Winkler, J. P. van Dijken, and J. T. Pronk. 2003. Overproduction of Threonine Aldolase Circumvents the Biosynthetic Role of Pyruvate Decarboxylase in Glucose-grown *Saccharomyces cerevisiae*. Appl. Environ. Microbiol. 69:2094-2099.
25. Verduyn, C., E. Postma, Wash. Scheffers, and J. P. van Dijken. 1990. Physiology of *Saccharomyces cerevisiae* in anaerobic glucose-limited chemostat cultures. J. Gen.Microbiol.136:395-403.
26. Verduyn, C., Ah. Stouthamer, Wash. Scheffers, and J. P. van Dijken. 1991. A theoretical evaluation of growth yields of yeasts. Antonie van Leeuwenhoek 59:49-63.
27. Verduyn, C., T. P. L. Zomerdijk, J. P. van Dijken, and W. A. Scheffers. 1992. Effect of benzoic acid on metabolic fluxes in yeasts: a continuous culture study on the regulation of respiration and alcoholic fermentation. Yeast 8:501-517.
28. Van Urk, H., Mak, P. R., Scheffers, Wash., van Dijken J. P. 1988. Metabolic responses of *Saccharomyces cerevisiae* CBS 8066 and *Candida utilis* CBS 621 upon transition from glucose limitation to glucose excess. Yeast 4:283-291.

What is claimed is:

1. A GCSI yeast strain having a deposit number NRRL Y-30651.

2. A GCSI yeast strain having a plasmid YEpLpLDH, wherein the GCSI yeast strain has a deposit number NRRL Y-30742.

3. A $C_2$ carbon source-independent yeast strain having a deposit number NRRL Y-30650.

* * * * *

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial
<220> FEATURE:
<223> OTHER INFORMATION: Synthetic oligonucleotide

<400> SEQUENCE: 1
tgacttatta tgtcaagcat                                                 20

<210> SEQ ID NO 2
<211> LENGTH: 23
<212> TYPE: DNA
<213> ORGANISM: Artificial
<220> FEATURE:
```

<223> OTHER INFORMATION: Synthetic oligonucleotide

<400> SEQUENCE: 2
atcgtatgaa atgattattt att                                            23

<210> SEQ ID NO 3
<211> LENGTH: 1117
<212> TYPE: DNA
<213> ORGANISM: lactate dehydrogenase gene of L. Plantarum
<220> FEATURE:
<221> NAME/KEY: misc_feature
<222> LOCATION: (14)..(14)
<223> OTHER INFORMATION: N = C, G, A, or T
<220> FEATURE:
<221> NAME/KEY: CDS
<222> LOCATION: (61)..(1023)

<400> SEQUENCE: 3
ggtaccacgc atgntgcaga cgcgttacgt atcggatcca gaattcgtga ttgacttatt    60 atg tca agc atg cca aat cat caa aaa gtt gtg tta gtc ggc gac ggc    108
Met Ser Ser Met Pro Asn His Gln Lys Val Val Leu Val Gly Asp Gly
1               5                   10                  15 gct gtt ggt tct agt tac gct ttt gcc atg gca caa caa gga att gct    156
Ala Val Gly Ser Ser Tyr Ala Phe Ala Met Ala Gln Gln Gly Ile Ala
            20                  25                  30 gaa gaa ttt gta att gtc gat gtt gtt aaa gat cgg aca aag ggt gac    204
Glu Glu Phe Val Ile Val Asp Val Val Lys Asp Arg Thr Lys Gly Asp
        35                  40                  45 gcc ctt gat ctt gaa gac gcc caa gca ttc acc gct ccc aag aag att    252
Ala Leu Asp Leu Glu Asp Ala Gln Ala Phe Thr Ala Pro Lys Lys Ile
    50                  55                  60 tac tca ggc gaa tat tca gat tgt aag gac gct gac tta gtt gtt att    300
Tyr Ser Gly Glu Tyr Ser Asp Cys Lys Asp Ala Asp Leu Val Val Ile
65                  70                  75                  80 aca gcc ggt gcg cct caa aag cct ggt gaa tca cgt tta gac tta gtt    348
Thr Ala Gly Ala Pro Gln Lys Pro Gly Glu Ser Arg Leu Asp Leu Val
                85                  90                  95 aac aag aat tta aat atc cta tca tcc att gtc aaa cca gtt gtt gac    396
Asn Lys Asn Leu Asn Ile Leu Ser Ser Ile Val Lys Pro Val Val Asp
            100                 105                 110 tcc ggc ttt gac ggc atc ttc tta gtt gct gct aac cct gtt gac atc    444
Ser Gly Phe Asp Gly Ile Phe Leu Val Ala Ala Asn Pro Val Asp Ile
        115                 120                 125 tta act tac gct act tgg aaa ttc tca ggt ttc cca aag gat cgt gtc    492
Leu Thr Tyr Ala Thr Trp Lys Phe Ser Gly Phe Pro Lys Asp Arg Val
    130                 135                 140 att ggt tca ggg act tcc tta gac tct tca cgt tta cgc gtt gcg tta    540
Ile Gly Ser Gly Thr Ser Leu Asp Ser Ser Arg Leu Arg Val Ala Leu
145                 150                 155                 160 ggc aaa caa ttc aat gtt gat cct cgt tcc gtt gat gct tac atc atg    588
Gly Lys Gln Phe Asn Val Asp Pro Arg Ser Val Asp Ala Tyr Ile Met
                165                 170                 175 ggt gaa cac ggt gat tct gaa ttt gct gct tac tca act gca acc atc    636
Gly Glu His Gly Asp Ser Glu Phe Ala Ala Tyr Ser Thr Ala Thr Ile
            180                 185                 190 ggg aca cgt cca gtt cgc gat gtc gct aag gaa caa ggc gtt tct gac    684
Gly Thr Arg Pro Val Arg Asp Val Ala Lys Glu Gln Gly Val Ser Asp
        195                 200                 205 gaa gat tta gcc aag tta gaa gat ggt gtt cgt aac aaa gct tac gac    732
Glu Asp Leu Ala Lys Leu Glu Asp Gly Val Arg Asn Lys Ala Tyr Asp
    210                 215                 220

```
atc atc aac ttg aag ggt gcc acg ttc tac ggt atc ggg act gct tta        780
Ile Ile Asn Leu Lys Gly Ala Thr Phe Tyr Gly Ile Gly Thr Ala Leu
225                 230                 235                 240 atg cgg att tcc aaa gcc att tta cgt gat gaa aat gcc gtt tta cca        828
Met Arg Ile Ser Lys Ala Ile Leu Arg Asp Glu Asn Ala Val Leu Pro
                245                 250                 255 gta ggt gcc tac atg gac ggc caa tac ggc tta aac gac att tat atc        876
Val Gly Ala Tyr Met Asp Gly Gln Tyr Gly Leu Asn Asp Ile Tyr Ile
            260                 265                 270 ggg act ccg gct gtg att ggt gga act ggt ttg aaa caa atc atc gaa        924
Gly Thr Pro Ala Val Ile Gly Gly Thr Gly Leu Lys Gln Ile Ile Glu
        275                 280                 285 tca cca ctt tca gct gac gaa ctc aag aag atg caa gat tcc gcc gca        972
Ser Pro Leu Ser Ala Asp Glu Leu Lys Lys Met Gln Asp Ser Ala Ala
    290                 295                 300 act ttg aaa aaa gtg ctt aac gac ggt tta gct gaa tta gaa aat aaa       1020
Thr Leu Lys Lys Val Leu Asn Asp Gly Leu Ala Glu Leu Glu Asn Lys
305                 310                 315                 320 taa tcatttcata cgatatctga attcgtcgac aagcttctcg agcctaggct            1073
agctctagac cacacgtgtg ggggcccgag ctcgcggccg ctgt                      1117
```

<210> SEQ ID NO 4
<211> LENGTH: 320
<212> TYPE: PRT
<213> ORGANISM: lactate dehydrogenase gene of L. Plantarum

<400> SEQUENCE: 4

```
Met Ser Ser Met Pro Asn His Gln Lys Val Val Leu Val Gly Asp Gly
1               5                   10                  15

Ala Val Gly Ser Ser Tyr Ala Phe Ala Met Ala Gln Gln Gly Ile Ala
            20                  25                  30

Glu Glu Phe Val Ile Val Asp Val Val Lys Asp Arg Thr Lys Gly Asp
        35                  40                  45

Ala Leu Asp Leu Glu Asp Ala Gln Ala Phe Thr Ala Pro Lys Lys Ile
    50                  55                  60

Tyr Ser Gly Glu Tyr Ser Asp Cys Lys Asp Ala Asp Leu Val Val Ile
65                  70                  75                  80

Thr Ala Gly Ala Pro Gln Lys Pro Gly Glu Ser Arg Leu Asp Leu Val
                85                  90                  95

Asn Lys Asn Leu Asn Ile Leu Ser Ser Ile Val Lys Pro Val Val Asp
            100                 105                 110

Ser Gly Phe Asp Gly Ile Phe Leu Val Ala Ala Asn Pro Val Asp Ile
        115                 120                 125

Leu Thr Tyr Ala Thr Trp Lys Phe Ser Gly Phe Pro Lys Asp Arg Val
    130                 135                 140

Ile Gly Ser Gly Thr Ser Leu Asp Ser Ser Arg Leu Arg Val Ala Leu
145                 150                 155                 160

Gly Lys Gln Phe Asn Val Asp Pro Arg Ser Val Asp Ala Tyr Ile Met
                165                 170                 175

Gly Glu His Gly Asp Ser Glu Phe Ala Ala Tyr Ser Thr Ala Thr Ile
            180                 185                 190

Gly Thr Arg Pro Val Arg Asp Val Ala Lys Glu Gln Gly Val Ser Asp
        195                 200                 205

Glu Asp Leu Ala Lys Leu Glu Asp Gly Val Arg Asn Lys Ala Tyr Asp
    210                 215                 220

Ile Ile Asn Leu Lys Gly Ala Thr Phe Tyr Gly Ile Gly Thr Ala Leu
```

```
-continued
225                 230                 235                 240

Met Arg Ile Ser Lys Ala Ile Leu Arg Asp Glu Asn Ala Val Leu Pro
            245                 250                 255

Val Gly Ala Tyr Met Asp Gly Gln Tyr Gly Leu Asn Asp Ile Tyr Ile
            260                 265                 270

Gly Thr Pro Ala Val Ile Gly Gly Thr Gly Leu Lys Gln Ile Ile Glu
        275                 280                 285

Ser Pro Leu Ser Ala Asp Glu Leu Lys Lys Met Gln Asp Ser Ala Ala
        290                 295                 300

Thr Leu Lys Lys Val Leu Asn Asp Gly Leu Ala Glu Leu Glu Asn Lys
305                 310                 315                 320
```